United States Patent
Nakada et al.

(10) Patent No.: US 6,538,137 B1
(45) Date of Patent: Mar. 25, 2003

(54) CYANOBIPHENYL DERIVATIVES

(75) Inventors: Tomohisa Nakada, Tokyo (JP); Takayuki Hara, Yamaguchi (JP); Yasunobu Takano, Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/959,769

(22) PCT Filed: May 17, 2000

(86) PCT No.: PCT/JP00/03169
§ 371 (c)(1),
(2), (4) Date: Nov. 7, 2001

(87) PCT Pub. No.: WO00/69811
PCT Pub. Date: Nov. 23, 2000

(30) Foreign Application Priority Data

May 17, 1999 (JP) .......................................... 11/135646

(51) Int. Cl.[7] ...................... C07D 211/12; C07C 255/50
(52) U.S. Cl. ........................ 546/227; 546/230; 558/416
(58) Field of Search .......................... 558/416; 546/229, 546/230, 227

(56) References Cited

U.S. PATENT DOCUMENTS 5,824,691 A   10/1998  Kuno et al.

FOREIGN PATENT DOCUMENTS

| EP | 1043310 A1 | * 10/2000 |
|---|---|---|
| EP | 1043310 | * 11/2000 |
| JP | 94/26709 | 11/1994 |
| JP | 99/26918 | 6/1999 |

OTHER PUBLICATIONS

International Search Report.

* cited by examiner

*Primary Examiner*—Joseph K. McKane
*Assistant Examiner*—Jennifer C. Murphy
(74) *Attorney, Agent, or Firm*—Sughrue Mion, PLLC

(57) ABSTRACT

Intermediates represented by the following formula:

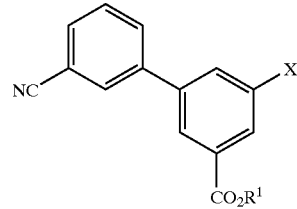

(wherein $R^1$ is a hydrogen atom, an alkyl group, an aryl group, an aralkyl group or the like; X is a carboxyl group, an alkoxycarbonyl group, an aryloxycarbonyl group, an aralkoxycarbonyl group, a formyl group, —$CH_2$—Y, —$CHZ_1Z_2$, —$CH(OR^4)OR^5$ or the like), in the synthesis of biphenylamidine derivatives to be used as inhibitors for an activated blood coagulation factor X, and a process for preparing the same.

10 Claims, No Drawings

CYANOBIPHENYL DERIVATIVES

This application is a 371 of PCT/JP00/03169 filed May 17, 2000.

TECHNICAL FIELD

The present invention relates to novel cyanobiphenyl derivatives and more particularly it relates to cyanobiphenyl derivatives or their salts useful as intermediates for biphenylamidine derivatives which are capable of providing selective inhibitors for an activated blood coagulation factor X (hereinafter abbreviated to "FXa") and a process for producing the same.

BACKGROUND ART

Thrombin inhibitors have been developed as antithrombotic agents in the past. Since these agents, however, inhibit the thrombin induced platelet aggregation as well as blood coagulation, therefore they have a risk of tendency towards bleeding as a side effect, it is difficult to control the extent of the anticoagulation.

DISCLOSURE OF THE INVENTION

The present inventors, therefore, have conducted intensive studies to find out anticoagulants based on the mode of action other than inhibition of thrombin which has a risk in such side effects. As a result of such effects, the inventors have found that biphenylamidine derivatives have excellent FXa inhibitory activity and can clinically be applied as an anticoagulant (WO99/26918).

Furthermore, the present inventors have continued studies on the biphenylamidine derivatives, then have found out novel compounds useful as intermediates for the biphenylamidine derivatives. The present invention has been accomplished on the basis of these findings.

That is, the present invention is cyanobiphenyl derivatives represented by the following general formula (1):

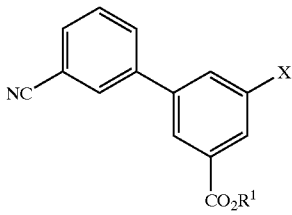

(1)

[wherein $R^1$ is a hydrogen atom, a $C_1$–$C_8$ alkyl group, an aryl group or an aralkyl group; X is a carboxyl group, a $C_1$–$C_8$ alkoxycarbonyl group, an aryloxycarbonyl group, an aralkoxycarbonyl group, a formyl group, the formula:

—CH$_2$—Y wherein Y is a chlorine atom, a bromine atom, an iodine atom, an azide group, —OR$^2$ (wherein $R^2$ is a hydrogen atom, a $C_1$–$C_8$ alkylsulfonyl group (the $C_1$–$C_8$ alkylsulfonyl group may further be substituted with a halogen atom)), an arylsulfonyl group or 4-piperidinomethyl group (a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group), or —NHR$^3$ (wherein R$^3$ is a hydrogen atom or 4-piperidinomethyl group (a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group), the formula:

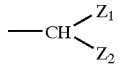

{wherein $Z_1$ and $Z_2$ are each independently a chlorine atom, a bromine atom or an iodine atom}, or the formula:

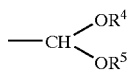

{wherein $R^4$ and $R^5$ are each independently a hydrogen atom, a $C_1$–$C_8$ alkyl group or a $C_1$–$C_8$ alkylcarbonyl group or both together may form a ring when $R^4$ and $R^5$ are each a $C_1$–$C_8$ alkyl group}], or their salts thereof (hereinafter referred to as the "cyanobiphenyl derivatives").

Further, the present invention is a process for preparing cyanobiphenyl derivatives represented by the following formula (3):

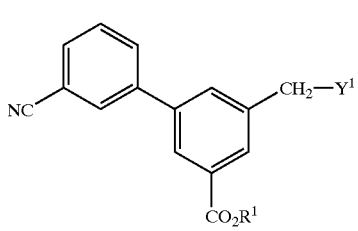

(3)

{wherein $R^1$ is as defined in the formula (2); $Y^1$ is —NHR$^3$ (wherein $R^3$ is 4-piperidinomethyl group (a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group))}, or their salts, which is carried out a condensation reaction of a compound represented by the following formula (2):

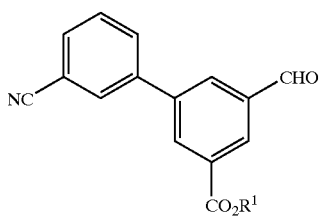

(2)

(wherein $R^1$ is a hydrogen atom, a $C_1$–$C_8$ alkyl group, an aryl group or an aralkyl group), with a compound represented by $Y^1$—H {wherein $Y^1$ is —NHR$^3$ (wherein $R^3$ is 4-piperidinomethyl group (a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group))}, and subsequent a reduction.

In addition, the present invention is a process for preparing cyanobiphenyl derivatives, represented by the following formula (5):

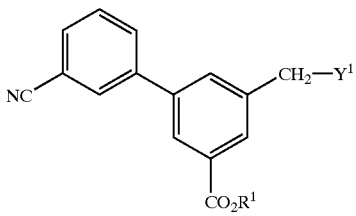
(5)

(wherein $R^1$ is as defined in the formula (4); $Y^1$ is as defined in the above formula (3)), or their salts, by reacting a compound represented by the following formula (4):

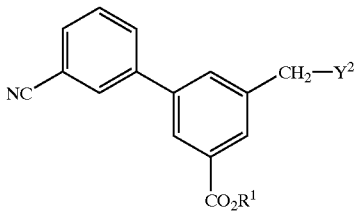
(4)

(wherein $R^1$ is a hydrogen atom, a $C_1$–$C_8$ alkyl group, an aryl group or an aralkyl group; $Y^2$ is a chlorine atom, a bromine atom or an iodine atom), with a compound represented by $Y^1$—H {wherein $Y^1$ is —$NHR^3$ (wherein $R^3$ is 4-piperidinomethyl group (a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group))}.

BEST MODE FOR CARRYING OUT THE INVENTION

The cyanobiphenyl derivatives of the present invention are represented by the above formula (1), wherein the definitions of substituents in the formula (1) are described as follows.

The "$C_1$–$C_8$ alkyl group" means a straight or a branched carbon chain having 1 to 8 carbon atoms, and include for example methyl group, ethyl group, propyl group, isopropyl group, butyl group, isobutyl group, sec-butyl group, tert-butyl group, pentyl group, neopentyl group, isopentyl group, 1,2-dimethylpropyl group, hexyl group, isohexyl group, 1,1-dimethylbutyl group, 2,2-dimethylbutyl group, 1-ethylbutyl group, 2-ethylbutyl group, isoheptyl group, octyl group, isooctyl group or the like. Among them, one having 1 to 4 carbon atoms is preferable, and methyl group or ethyl group is especially preferable.

The "aryl group" means a carbocyclic aromatic group including for example phenyl group or naphthyl group, etc. or a heteroaryl group including for example pyridyl group or furyl group, etc., and phenyl group is preferable.

The "aralkyl group" means benzyl group, phenethyl group, phenylpropyl group, 1-naphthylmethyl group, 2-naphthylmethyl group or the like, and benzyl group is preferable.

The "$C_1$–$C_8$ alkoxycarbonyl group" means an alkoxycarbonyl group having a straight or a branched carbon chain having 1 to 8 carbon atoms, and includes for example methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, neopentyloxycarbonyl group, hexyloxycarbonyl group, heptyloxycarbonyl group, octyloxycarbonyl group or the like. The "$C_1$–$C_8$ alkoxycarbonyl group" is preferably methoxycarbonyl group or ethoxycarbonyl group.

The "aryloxycarbonyl group" means phenoxycarbonyl group, naphthyloxycarbonyl group, 4-methylphenoxycarbonyl group, 3-chlorophenoxycarbonyl group, 4-methoxyphenoxycarbonyl group or the like, and phenoxycarbonyl group is preferable.

The "aralkoxycarbonyl group" means benzyloxycarbonyl group, 4-methoxybenzyloxycarbonyl group, 3-trifluoromethylbenzyloxycarbonyl group, 3-oxohydroisobenzofuranyloxycarbonyl group or like, and benzyloxycarbonyl group is preferable.

The "$C_1$–$C_8$ alkylsulfonyl group" means a sulfonyl group having a straight or a branched carbon chain having 1 to 8 carbon atoms, and includes, for example, methylsulfonyl group, ethylsulfonyl group, butylsulfonyl group, hexylsulfonyl group, octylsulfonyl group, propylsulfonyl group, isopropylsulfonyl group, isobutylsulfonyl group, sec-butylsulfonyl group, tert-butylsulfonyl group, pentylsulfonyl group, heptylsulfonyl group or the like, and methylsulfonyl group is preferable. The alkyl group moiety may further be substituted with a halogen atom, and the "$C_1$–$C_8$ alkylsulfonyl group" includes for example tifluoromethylsulfonyl group, 2,2,2-trifluoroethylsulfonyl group, trichloromethylsulfonyl group, dichloromethylsulfonyl group, monochloromethylsulfonyl group or the like. Trifluoromethylsulfonyl group is preferable.

The "arylsulfonyl group" means benzenesulfonyl group, p-toluenesulfonyl group, 4-nitrobenzenesulfonyl group, 1-naphthylsulfonyl group, 8-quinolinesulfonyl group or the like, and p-toluenesulfonyl group is preferable.

The "$C_1$–$C_8$ alkyl group" substituted at the nitrogen atom in the 4-piperidinomethyl group means a straight or a branched carbon chain having 1 to 8 carbon atoms, and includes for example methyl group, ethyl group, propyl group, isopropyl group, butyl group, isobutyl group, sec-butyl group, tert-butyl group, pentyl group, neopentyl group, isopentyl group, 1,2-dimethylpropyl group, hexyl group, isohexyl group, 1,1-dimethylbutyl group, 2,2-dimethylbutyl group, 1-ethylbutyl group, 2-ethylbutyl group, isoheptyl group, octyl group, isooctyl group or the like. The "$C_1$–$C_8$ alkyl group" is preferably methyl group, ethyl group or isopropyl group.

The "$C_1$–$C_8$ alkylcarbonyl group" substituted at the nitrogen atom in the 4-piperidinomethyl group means a carbonyl group having a straight or a branched carbon chain having 1 to 8 carbon atoms, and includes for example acetyl group, propionyl group, butyryl group, isobutyryl group, valeryl group, isovaleryl group, pivaloyl group, hexanoyl group, heptanoyl group, octanoyl group or the like. The "$C_1$–$C_8$ alkylcarboinyl group" is preferably acetyl group.

The "arylcarbonyl group" substituted at the nitrogen atom in the 4-piperidinomethyl group means benzoyl group, 4-methoxybenzoyl group or 3-trifluoromethylbenzoyl group and the like or a carbonyl group to which a heteroaryl group is bound such as 2-furylcarbonyl group, 3-pyridylcarbonyl group and the like. The "arylcarbonyl group" is preferably benzoyl group.

The "$C_1-C_8$ alkoxycarbonyl group" substituted at the nitrogen atom in the 4-piperidinomethyl group means an alkoxycarbonyl group having a straight or a branched carbon chain having 1 to 8 carbon atoms, and includes for example methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, neopentyloxycarbonyl group, hexyloxycarbonyl group, heptyloxycarbonyl group, octyloxycarbonyl group and the like. The $C_1-C_8$ alkoxycarbonyl group" is preferably methoxycarbonyl group, ethoxycarbonyl group or tert-butoxycarbonyl group.

The "$C_5-C_8$ alkoxycarbonyl group" substituted at the nitrogen atom in the 4-piperidinomethyl group means an alkoxycarbonyl group having a straight or branched carbon chain having 5 to 8 carbon atoms, and includes for example pentyloxycarbonyl group, isopentyloxycarbonyl group, neopentyloxycarbonyl group, cyclopentyloxycarbonyl group, hexyloxycarbonyl group, cyclohexyloxycarbonyl group, heptyloxycarbonyl group, octyloxycarbonyl group, 2-ethylhexyloxycarbonyl group and the like. The "$C_5-C_8$ alkoxycarbonyl group" is preferably pentyloxycarbonyl group, hexyloxycarbonyl group, heptyloxycarbonyl group or octyloxycarbonyl group.

The "aryloxycarbonyl group" substituted at the nitrogen atom in the 4-piperidinomethyl group means phenoxycarbonyl group, naphthyloxycarbonyl group, 4-methylphenoxycarbonyl group, 3-chlorophenoxycarbonyl group, 4-methoxyphenoxycarbonyl group and the like. The "aryloxycarbonyl group" is preferably phenoxycarbonyl group.

The aralkoxycarbonyl group" substituted at the nitrogen atom in the 4-piperidinomethyl group means benzyloxycarbonyl group, 4-methoxybenzyloxycarbonyl group, 3-trifluoromethylbenzyloxycarbonyl group, 3-oxohydroisobenzofuranyloxycarbonyl group and the like. The "aralkoxycarbonyl group" is preferably benzyloxycarbonyl group.

The "$C_1-C_8$ alkyl group" in $R^4$ and $R^5$ means a straight or a branched carbon chain having 1 to 8 carbon atoms, and includes for example, methyl group, ethyl group, propyl group, isopropyl group, butyl group, isobutyl group, sec-butyl group, tert-butyl group, pentyl group, neopentyl group, isopentyl group, 1,2-dimethylpropyl group, hexyl group, isohexyl group, 1,1-dimethylbutyl group, 2,2-dimethylbutyl group, 1-ethylbutyl group, 2-ethylbutyl group, isoheptyl group, octyl group, isooctyl group and the like. The "$C_1-C_8$ alkyl group" is preferably methyl group or ethyl group. In the case wherein $R^4$ and $R^5$ together form a ring, it includes for example ethylene group, propylene group, 2-methylenepropylene group, 2,2-dibromopropylene group and the like, and ethylene group or propylene group is preferable.

The "$C_1-C_8$ alkylcarbonyl group" in $R^4$ and $R^5$ means a carbonyl group having a straight-chain or a branched carbon chain having 1 to 8 carbon atoms, and includes for example acetyl group, propionyl group, butyryl group, isobutyryl group, valeryl group, isovaleryl group, pivaloyl group, hexanoyl group, heptanoyl group, octanoyl group and the like. The "$C_1-C_8$ alkylcarbonyl group" is preferably acetyl group.

The cyanobiphenyl derivatives of the present invention may form acid addition salts, and may form salts with bases depending on the species of the substituents. These salts are not especially restricted insofar as these salts are pharmaceutically acceptable, and include for example mineral salts such as hydrochloride, hydrobromide, hydroiodide, phosphate, nitrate or sulfate, organic sulfonates such as methanesulfonate, 2-hydroxyethanesulfonate or p-toluenesulfonate, organic carboxylates such as acetate, trifluoroacetate, propionate, oxalate, malonate, succinate, glutarate, adipate, tartrate, maleate, malate or mandelate, salts with inorganic bases such as sodium salts, potassium salts, magnesium salts, calcium salts or aluminum salts, or salts with organic bases such as methylamine salts, ethylamine salts, lysine salts or ornithine salts.

The preferred range of the cyanobiphenyl derivatives of the present invention is as follows.

In the compounds represented by the above formula (1), cyanobiphenyl derivatives [wherein $R^1$ is a hydrogen atom or a $C_1-C_8$ alkyl group in the above definition, and, in the above definition, X is a $C_1-C_8$ alkoxycarbonyl group, a formyl group, the formula:

—CH$_2$—Y

{wherein, in the above definition, Y is a chlorine atom, a bromine atom, an iodine atom, an azide group, —OR$^2$ (wherein, in the above definition, R$^2$ is a hydrogen atom or 4-piperidinomethyl group (a nitrogen atom in the 4-piperidinomethyl group may be substituted with a $C_1-C_8$ alkyl group, a $C_1-C_8$ alkylcarbonyl group, an arylcarbonyl group, a $C_1-C_8$ alkoxycarbonyl group, an aryloxycarbonyl group or an aralkoxycarbonyl group)) or —NHR$^3$ (wherein R$^3$ is as defined as above)}, the formula:

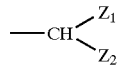

{wherein $Z_1$ and $Z_2$ are each as defined above}, or the formula:

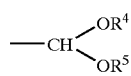

{wherein $R^4$ and $R^5$ are each as defined as above}], or their salts thereof.

The more preferred range is as follows.

In the compounds represented by the above formula (1), the cyanobiphenyl derivatives [wherein $R^1$ is a hydrogen atom or a $C_1-C_8$ alkyl in the above definition and, in the above definition, X is a formyl group or the formula:

—CH$_2$—Y

{wherein, in the above definition, Y is a chlorine atom, a bromine atom, an iodine atom, —OR$^2$ (wherein, in the above definition, R$^2$ is a hydrogen atom or 4-piperidinomethyl group (a nitrogen atom in the 4-piperidinomethyl group may be substituted with a $C_1-C_8$ alkyl group, a $C_1-C_8$ alkylcarbonyl group, an arylcarbonyl group, a $C_1-C_8$ alkoxycarbonyl group, an aryloxycarbonyl group or an aralkoxycarbonyl group)), or —NHR$^3$ (wherein, in the above definition, R$^3$ is 4-piperidinomethyl group (a nitrogen atom in the 4-piperidinomethyl group may be substituted with a $C_1-C_8$ alkyl group, a $C_1-C_8$ alkylcarbonyl group, an arylcarbonyl group, a $C_1-C_8$ alkoxycarbonyl group, an aryloxycarbonyl group or an aralkoxycarbonyl group))}], or their salts thereof.

The far more preferred range is as follows:

In the compounds represented by the above formula (1), the cyanobiphenyl derivatives [wherein $R^1$ is a hydrogen atom or a $C_1$–$C_8$ alkyl group in the above definition and, in the above definition, X is a formyl group or the formula:

—$CH_2$—Y

{wherein, in the above definition, Y is a chlorine atom, a bromine atom, an iodine atom, —$OR^2$ (wherein, in the above definition, $R^2$ is hydrogen atom, that is, —$OR^2$ is a hydroxyl group), or —$NHR^3$ (wherein, in the above definition, $R^3$ is 4-piperidinomethyl group (a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group))}], or their salts thereof.

Examples of the cyanobiphenyl derivatives or their salts of the presence invention are shown in the following table.

-continued

| No. | R¹ | X |
|---|---|---|
| 27 | H | CH₂—NH—CH₂—[4-piperidinyl]-N-C(=O)-CH₂CH₂CH₂CH₃ |
| 28 | H | CH₂—NH—CH₂—[4-piperidinyl]-N-C(=O)-(CH₂)₄CH₃ |
| 29 | H | CH₂—NH—CH₂—[4-piperidinyl]-N-C(=O)-(CH₂)₅CH₃ |
| 30 | H | CH₂—NH—CH₂—[4-piperidinyl]-N-C(=O)-(CH₂)₆CH₃ |
| 31 | H | CH₂—NH—CH₂—[4-piperidinyl]-N-C(=O)-C₆H₅ |
| 32 | H | CH₂—NH—CH₂—[4-piperidinyl]-N-C(=O)-O-CH₃ |
| 33 | H | CH₂—NH—CH₂—[4-piperidinyl]-N-C(=O)-O-CH₂CH₃ |
| 34 | H | CH₂—NH—CH₂—[4-piperidinyl]-N-C(=O)-O-CH₂CH₂CH₃ |
| 35 | H | CH₂—NH—CH₂—[4-piperidinyl]-N-C(=O)-O-CH(CH₃)₂ |
| 36 | H | CH₂—NH—CH₂—[4-piperidinyl]-N-C(=O)-O-CH₂CH₂CH₂CH₃ |
| 37 | H | CH₂—NH—CH₂—[4-piperidinyl]-N-C(=O)-O-CH₂CH(CH₃)₂ |
| 38 | H | CH₂—NH—CH₂—[4-piperidinyl]-N-C(=O)-O-CH(CH₃)CH₂CH₃ |
| 39 | H | CH₂—NH—CH₂—[4-piperidinyl]-N-C(=O)-O-C(CH₃)₃ |
| 40 | H | CH₂—NH—CH₂—[4-piperidinyl]-N-C(=O)-O-C₆H₅ |
| 41 | H | CH₂—NH—CH₂—[4-piperidinyl]-N-C(=O)-O-CH₂-C₆H₅ |
| 42 | Me | CHO |
| 43 | Me | CH₂—Cl |
| 44 | Me | CH₂—Br |
| 45 | Me | CH₂—I |
| 46 | Me | CH₂—OH |
| 47 | Me | CH₂—NH—CH₂—[4-piperidinyl]-NH |
| 48 | Me | CH₂—NH—CH₂—[4-piperidinyl]-N-CH₃ |
| 49 | Me | CH₂—NH—CH₂—[4-piperidinyl]-N-CH₂CH₃ |
| 50 | Me | CH₂—NH—CH₂—[4-piperidinyl]-N-CH₂CH₂CH₃ |
| 51 | Me | CH₂—NH—CH₂—[4-piperidinyl]-N-CH(CH₃)₂ |
| 52 | Me | CH₂—NH—CH₂—[4-piperidinyl]-N-CH₂CH₂CH₂CH₃ |
| 53 | Me | CH₂—NH—CH₂—[4-piperidinyl]-N-CH₂CH(CH₃)₂ |
| 54 | Me | CH₂—NH—CH₂—[4-piperidinyl]-N-CH(CH₃)CH₂CH₃ |
| 55 | Me | CH₂—NH—CH₂—[4-piperidinyl]-N-C(CH₃)₃ |
| 56 | Me | CH₂—NH—CH₂—[4-piperidinyl]-N-(CH₂)₄CH₃ |

-continued
| No. | R¹ | X |
|---|---|---|
| 57 | Me | 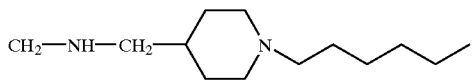 |
| 58 | Me | |
| 59 | Me | |
| 60 | Me | |
| 61 | Me | |
| 62 | Me | |
| 63 | Me | |
| 64 | Me | |
| 65 | Me | |
| 66 | Me | |
| 67 | Me | |
| 68 | Me | |
-continued
| No. | R¹ | X |
|---|---|---|
| 69 | Me | 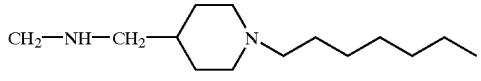 |
| 70 | Me | |
| 71 | Me | |
| 72 | Me | |
| 73 | Et | |
| 74 | Et | |
| 75 | Et | |
| 76 | Me | |
| 77 | Me | |
| 78 | Me | |
| 79 | Me | |
| 80 | Me | |

-continued
| No. | R¹ | X |
|---|---|---|
| 81 | Me | 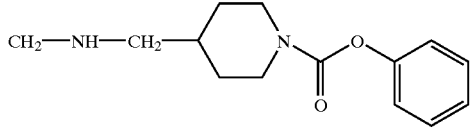 |
| 82 | Me | 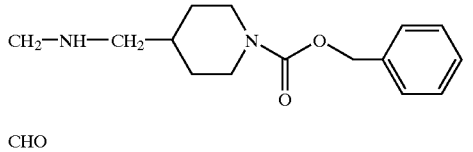 |
| 83 | Et | CHO |
| 84 | Et | CH₂—Cl |
| 85 | Et | CH₂—Br— |
| 86 | Et | CH₂—I |
| 87 | Et | CH₂—OH |
| 88 | Et | 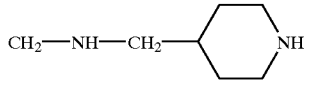 |
| 89 | Et | 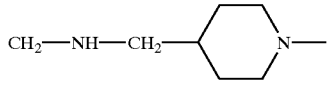 |
| 90 | Et | 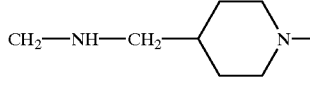 |
| 91 | Et | 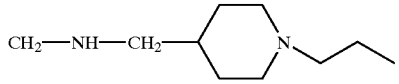 |
| 92 | Et | 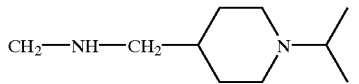 |
| 93 | Et | 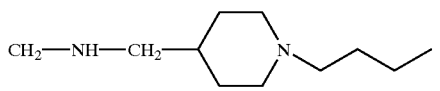 |
| 94 | Et | 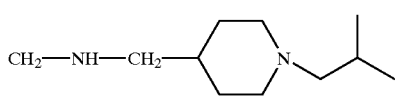 |
| 95 | Et | 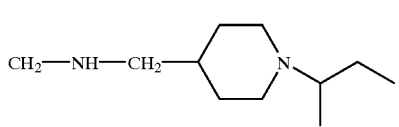 |
| 96 | Et | 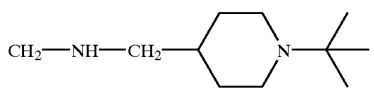 |
| 97 | Et | 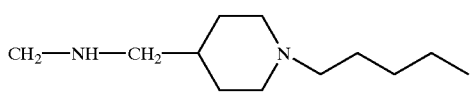 |
| 98 | Et | 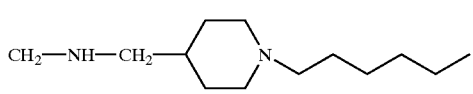 |
-continued
| No. | R¹ | X |
|---|---|---|
| 99 | Et | 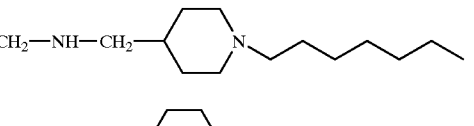 |
| 100 | Et | 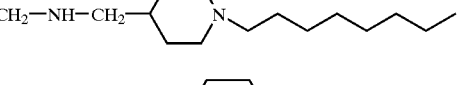 |
| 101 | Et | 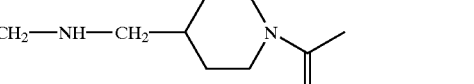 |
| 102 | Et | 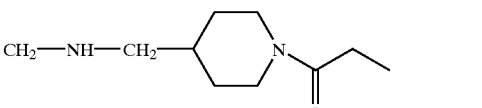 |
| 103 | Et | 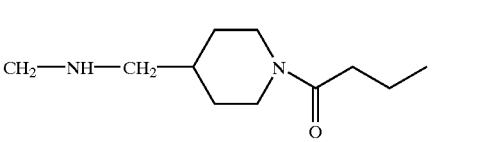 |
| 104 | Et | 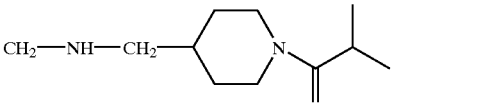 |
| 105 | Et | 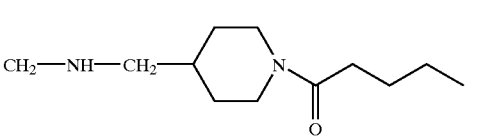 |
| 106 | Et | 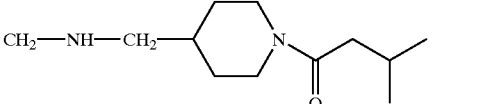 |
| 107 | Et | 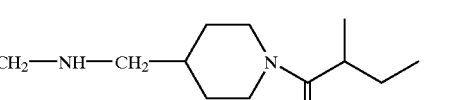 |
| 108 | Et | 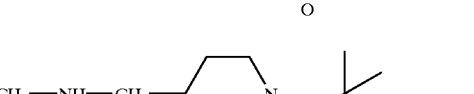 |
| 109 | Et | 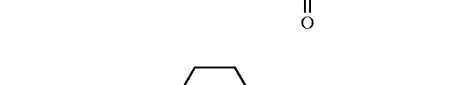 |
| 110 | Et | 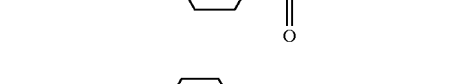 |

-continued

| No. | R¹ | X |
|---|---|---|
| 111 | Et | CH₂—NH—CH₂—[piperidine]-N-C(=O)-hexyl |
| 112 | Et | CH₂—NH—CH₂—[piperidine]-N-C(=O)-heptyl |
| 113 | Et | CH₂—NH—CH₂—[piperidine]-N-C(=O)-phenyl |
| 114 | Et | CH₂—NH—CH₂—[piperidine]-N-C(=O)-OCH₃ |
| 115 | Et | CH₂—NH—CH₂—[piperidine]-N-C(=O)-OEt |
| 116 | Et | CH₂—NH—CH₂—[piperidine]-N-C(=O)-O-propyl |
| 117 | Et | CH₂—NH—CH₂—[piperidine]-N-C(=O)-O-isopropyl |
| 118 | Et | CH₂—NH—CH₂—[piperidine]-N-C(=O)-O-butyl |
| 119 | Et | CH₂—NH—CH₂—[piperidine]-N-C(=O)-O-isobutyl |
| 120 | Et | CH₂—NH—CH₂—[piperidine]-N-C(=O)-O-sec-butyl |
| 121 | Et | CH₂—NH—CH₂—[piperidine]-N-C(=O)-O-tert-butyl |
| 122 | Et | CH₂—NH—CH₂—[piperidine]-N-C(=O)-O-phenyl |

-continued

| No. | R¹ | X |
|---|---|---|
| 123 | Et | CH₂—NH—CH₂—[piperidine]-N-C(=O)-O-CH₂-phenyl |

Among the compounds listed in the above table, compound Nos. 42, 44, 46, 47, 48, 51, 60, 73, 80, 83, 85, 87, 88, 89, 92, 101, 114 and 121 are preferred, and compound Nos. 42, 44, 46, 47, 51, 60 and 80 are more preferred.

Furthermore, the most preferred range of the cyanobiphenyl derivatives of the present invention is as follows.

Cyanobiphenyl derivatives [wherein, $R^1$ is hydrogen atom or a $C_1$–$C_8$ alkyl group in the above definition, and, in the above definition, X is the formula:

$$—CH_2—Y$$

{wherein, in the above definition, Y is —$NHR^3$ (wherein, in the above definition, $R^3$ is 4-piperidinomethyl group (a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group))}], or their salts thereof.

Among the compounds listed in the above table, compound Nos. 47 and 80 are most preferred.

On the other hand, the following cyanobiphenyl derivatives are also within the preferred range of the present invention.

That is, cyanobiphenyl derivatives [wherein, in the above formula (1), $R^1$ is as defined above, and X is, in the above definition, a carboxyl group, a $C_1$–$C_8$ alkoxycarbonyl group, an aryloxycarbonyl group, an aralkoxycarbonyl group, a formyl group, the formula:

$$—CH_2—Y$$

{wherein, in the above definition, Y is a chlorine atom, an iodine atom, —$OR^2$ (wherein, in the above definition, $R^2$ is a $C_1$–$C_8$ alkylsulfonyl group (the $C_1$–$C_8$ alkylsulfonyl group may further be substituted with halogen atoms)), an arylsulfonyl group or 4-piperidinomethyl group (a nitrogen atom in the 4-piperidinomethyl group is substituted with a $C_5$–$C_8$ alkoxycarbonyl group or an aryloxycarbonyl group), —$NHR^3$ (wherein, in the above definition, $R^3$ is 4-piperidinomethyl group (a nitrogen atom in the 4-piperidinomethyl group is substituted with a $C_5$–$C_8$ alkoxycarbonyl group or an aryloxycarbonyl group)), the formula:

$$—CH{<}^{Z_1}_{Z_2}$$

{wherein $Z_1$ and $Z_2$ are each as defined above}, or the formula:

$$—CH{<}^{OR^4}_{OR^5}$$

{wherein $R^4$ and $R^5$ are each as defined above}], or their salts thereof.

The more preferred range is as follows.

That is, in the above formula (1), $R^1$ is, in the above definition, a hydrogen atom or a $C_1$–$C_8$ alkyl group, and X is, in the above definition, a carboxyl group, a $C_1$–$C_8$ alkoxycarbonyl group, a formyl group, or the formula:

—CH$_2$—Y

{wherein Y is, in the above definition, —OR$^2$ (wherein $R^2$ is 4-piperidinomethyl group (a nitrogen atom in the 4-piperidinomethyl group is substituted with a $C_5$–$C_8$ alkoxycarbonyl group or an aryloxycarbonyl group)), —NHR$^3$ ($R^3$ is, in the above definition, 4-piperidinomethyl group (a nitrogen atom in the 4-piperidinomethyl group is substituted with a $C_1$–$C_8$ alkoxycarbonyl group or an aryloxycarbonyl group))}, or their salts thereof.

The far more preferred range is as follows.

Cynobiphenyl derivatives [wherein, in the above formula (1), $R^1$ is, in the above definition, a hydrogen atom or a $C_1$–$C_8$ alkyl group, and X is, in the above definition, a formyl group or the formula:

—CH$_2$—Y

{wherein, in the above definition, Y is —NHR$^3$ (wherein, in the above definition, $R^3$ is 4-piperidinomethyl group (a nitrogen atom in the 4-piperidinomethyl group is substituted with a $C_5$–$C_8$ alkoxycarbonyl group or an aryloxycarbonyl group))}], or their salts thereof Among these compounds, the following compounds are especially preferred. Methyl 3-(3-cyanophenyl)-5-formylbenzoate, methyl 3-(3-cyanophenyl)-5-[((N-n-pentyloxycarbonyl)piperidin-4-ylmethyl)aminomethyl] benzoate, methyl 3-(3-cyanophenyl)-5-[((N-n-hexyloxycarbonyl)piperidin-4-ylmethyl]aminomethyl] benzoate, methyl 3-(3-cyanophenyl)-5-[((N-n-heptyloxycarbonyl)piperidin-4-ylmethyl)aminomethyl] benzoate, methyl 3-(3-cyanophenyl)-5-[((N-n-octyloxycarbonyl)piperidin-4-ylmethyl]aminomethyl] benzoate and methyl 3-(3-cyanophenyl)-5-[((N-phenoxycarbonyl)piperidin-4-ylmethyl)aminomethyl] benzoate.

Among the compounds listed above, methyl 3-(3-cyanophenyl)-5-formylbenzoate is further more preferred.

A representative process for synthesizing the cyanobiphenyl derivatives of the present invention is detailed in the following description.

In the present invention, when starting materials or intermediates have substituents which may influence the reaction such as a hydroxyl group, an amino group or a carboxyl group, it is preferable to suitably protect such functional groups to carry out the objective reaction and then eliminate the protecting groups. The protecting group is not especially limited if it is the one which is usually used for each of substituents without adverse effects on other moieties in protecting and deprotecting steps. It includes, for example, a trialkylsilyl group, a $C_1$–$C_4$ alkoxymethyl group, a tetrahydropyranyl group, an acyl group and a $C_1$–$C_4$ alkoxycarbonyl group as a protecting group of a hydroxyl group. It includes, for example, a $C_1$–$C_4$ alkoxycarbonyl group, a benzyloxycarbonyl group and an acyl group as a protecting group of an amino group. It includes, for example, a $C_1$–$C_4$ alkyl group as the protecting group of a carboxyl group. The deprotecting reaction can be carried out according to methods usually conducted for respective protecting groups.

The cyanobiphenyl derivatives of the present invention can be synthesized according to, for example, the following reaction formula (a):

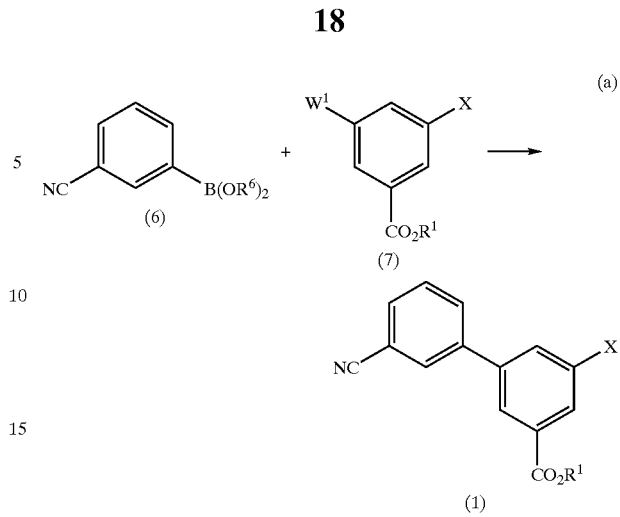

wherein $R^1$ is as defined in the above formula (1), $R^6$ is a hydrogen atom or a $C_1$–$C_4$ alkyl group and $W^1$ is a chlorine atom, a bromine atom, an iodine atom or a trifluoromethylsulfonyloxy group.

That is, cyanophenylboronic acid derivatives (6) which are precursors are reacted with aryl halides or aryl trifluoromethylsulfonates (7) in the presence of a base and a transition metal catalyst such as palladium or nickel and, if necessary, a phase-transfer catalyst to thereby produce the cyanobiphenyl derivatives of the present invention.

Ethers such as tetrahydrofuran, 1,4-dioxane or dimethoxyethane, hydrocarbons such as benzene or toluene, halogenated hydrocarbons such as dichloromethane or chloroform, alcohols such as methanol or ethanol, acetonitrile, dimethylformamide, water or the like or mixed solvents thereof are used as the solvent usually used in this reaction.

Inorganic bases such as potassium carbonate or sodium carbonate, alkoxides such as tert-butoxypotassium and organic tertiary amines such as triethylamine or pyridine are used as the base used in the reaction.

A zerovalent palladium such as tetrakis(triphenylphosphine)palladium, a bivalent palladium such as palladium acetate or diphenylphosphinobutanepalladium dichloride, a bivalent nickel such as [bis(diphenylphosphino)ferrocene]nickel dichloride and the like are used in an amount of 0.001 to 100 mol % as the transition metal catalysts, and tetra-$C_1$–$C_8$ alkylammonium halides or the like in an amount of 0.001 to 100 mol % is used as the phase-transfer catalysts in combination.

Among them, a combination of dimethylformamide as the solvent with potassium carbonate as the base and zerovalent palladium such as tetrakis(triphenylphosphine)palladium as the transition metal catalyst or a combination of water as the solvent, potassium carbonate as the base, palladium acetate as the transition metal catalyst and tetrabutylammonium bromide as the phase-transfer catalyst or a combination of a mixed solvent of toluene-methanol as the solvent, potassium carbonate as the base and palladium acetate as the transition metal catalyst is preferred. The reaction is usually carried out at room temperature or under heating for 0.1 to 100 hours.

When X is represented by —CH$_2$—Y$^2$ described below in the cyanobiphenyl derivatives of the present invention, the cyanobiphenyl derivatives can be synthesized even according to, for example, the following reaction formula (b):

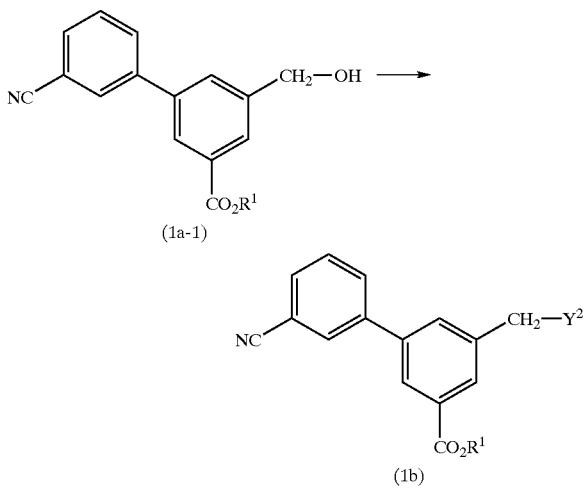

wherein $R^1$ is as defined in the above formula (1), and $Y^2$ is a chlorine atom, a bromine atom or an iodine atom.

That is, the cyanobiphenyl derivatives (1a-1) prepared according to the above reaction formula (a) are reacted with halogenating agents in the presence or absence of bases to thereby produce the cyanobiphenyl derivatives (1b) which are the compounds of the present invention.

Ethers such as tetrahydrofuran or diethyl ether, hydrocarbons such as toluene or hexane, halogenated hydrocarbons such as dichloromethane or chloroform or mixed solvents thereof are used as the solvent usually used in the reaction.

Inorganic bases such as potassium carbonate or sodium carbonate or organic tertiary amines such as triethylamine or pyridine are used as the base. Furthermore, phosphorus trihalides, phosphorus pentahalides, thionyl halides and the like are used as the halogenating agents. The reaction is usually carried out at room temperature or under heating for 0.5 to 100 hours.

Among them, a combination of diethyl ether as the solvent with phosphorus tribromide as the halogenating agent is preferred.

When X is represented by —CH$_2$—Y$^3$ described below in the cyanobiphenyl derivatives of the present invention, the cyanobiphenyl derivatives can be synthesized even according to, for example, the following reaction formula (c):

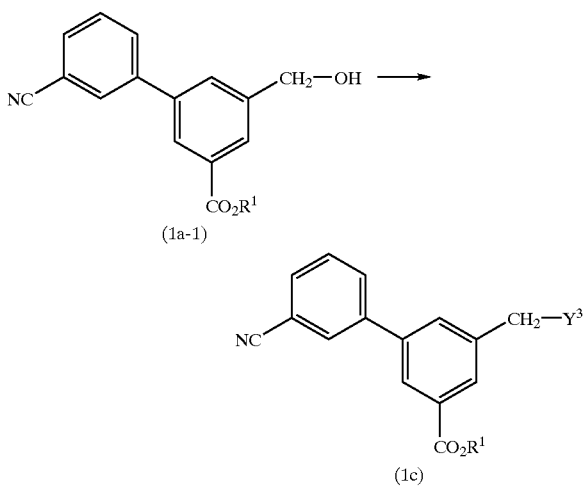

wherein $R^1$ is as defined in the above formula (1), and $Y^3$ is —OR$^2$ (wherein $R^2$ may be substituted with a $C_1$–$C_8$ alkylsulfonyl group (the alkyl group may further be substituted with halogen atoms) or an arylsulfonyl group).

That is, the cyanobiphenyl derivatives (1a-1) prepared according to the above reaction formula (a) are reacted with sulfonyl halides or sulfonic acid anhydrides in the presence of bases to thereby produce the cyanobiphenyl derivatives (1c), which are the compounds of the present invention.

Ethers such as tetrahydrofuran or diethyl ether, hydrocarbons such as toluene or hexane, halogenated hydrocarbons such as dichloromethane or chloroform, or mixed solvents thereof are used as the solvent usually used in the reaction.

Sulfonyl halides such as methylsulfonyl chloride, p-toluenesulfonyl chloride and the like and sulfonic acid anhydrides such as methylsulfonic acid anhydride, trifluoromethylsulfonic acid anhydride and the like are used.

Inorganic bases such as potassium carbonate or sodium carbonate or organic tertiary amines such as triethylamine or pyridine are used as the base.

The reaction is usually carried out at room temperature, under cooling with ice or under heating for 0.5 to 100 hours.

When X is represented by —CH$_2$—Y$^1$ described below in the cyanobiphenyl derivatives of the present invention, the cyanobiphenyl derivatives can be synthesized even according to, for example, the following reaction formula (d):

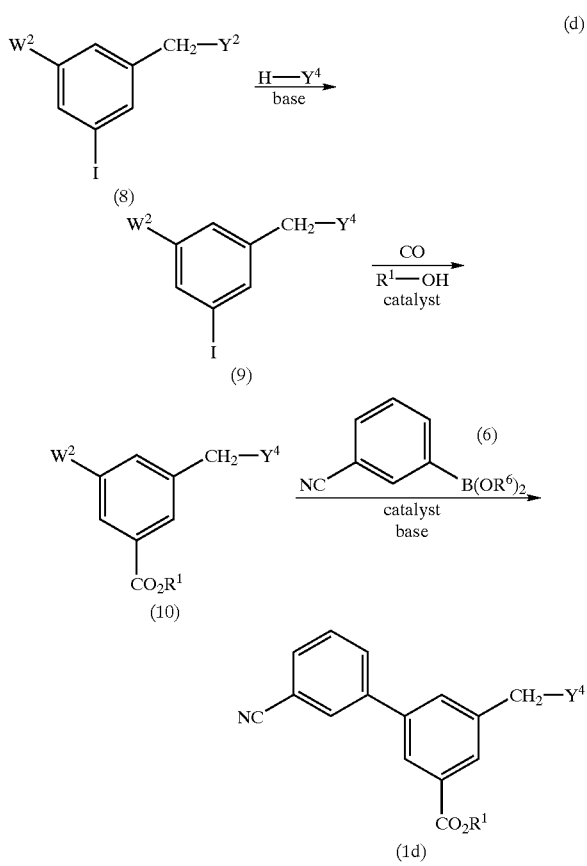

wherein $R^1$ is as defined in the formula (1), $Y^2$ and $R^6$ are each as defined in the above reaction formulae (a) and (b), $Y^4$ is —OR$^2$ (wherein $R^2$ is 4-piperidinomethyl group (a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group)), and $W^2$ is a bromine atom or a trifluoromethylsulfonyloxy group.

That is, iodobenzene derivatives (8), which are starting materials, are mixed with alcohols represented by $Y^4$—H in the presence of bases to provide ether derivatives (9), which are then monocarbonylated to introduce a substituent group $CO_2R^1$. Thereby, benzoic acid derivatives (10) are obtained. Further, a coupling reaction with cyanophenylboronic acid derivatives (6) are carried out to produce cyanobiphenyl derivatives (1d) which are the compounds of the present invention.

The etherification shown in the first step of the reaction formula (d) is carried out by using ethers such as tetrahydrofuran or diethyl ether, hydrocarbons such as benzene or toluene, aprotic polar solvents such as dimethylformamide or hexamethylphosphoric triamide or mixed solvents and the like thereof. Metal oxides such as barium oxide or zinc oxide, metal hydroxides such as sodium hydroxide or potassium hydroxide, metal hydrides such as sodium hydride and the like are used as such a base. The reaction usually proceeds at 0 to 100° C. for 3 to 72 hours with stirring. The reaction is preferably carried out at 20 to 80° C. for 8 to 36 hours by using sodium hydride in anhydrous ethers such as tetrahydrofuran or diethyl ether.

The reaction for introducing the substituent group $CO_2R^1$ shown in the second step of the reaction formula (d) can be carried out by dissolving the ether derivatives (9) obtained in the first step in alcohols represented by $R^1$—OH, adding bivalent palladium catalysts and bases such as tertiary amines, for example, triethylamine and, if necessary, phosphine ligands such as triphenylphosphine and stirring the resulting mixture at room temperature or under heating in an atmosphere of carbon monoxide for 3 to 48 hours to convert the iodine atom into the group $CO_2R^1$. The reaction is preferably carried out at 60 to 80° C. for 12 to 36 hours by using bistriphenylphosphinepalladium chloride or palladium acetate as the catalyst, diisopropylethylamine or tributylaluminum as the base and methanol as the solvent.

The coupling reaction shown in the third step of the reaction formula (d) is carried out by reacting benzoic acid derivatives (10) with cyanophenylboronic acid derivatives (6) in the presence of transition metal catalysts to thereby produce the cyanobiphenyl derivatives (id) which are the compounds of the present invention.

Ethers such as tetrahydrofuran, 1,4-dioxane or dimethoxyethane, hydrocarbons such as benzene or toluene, halogenated hydrocarbons such as dichloromethane or chloroform, alcohols such as methanol or ethanol, acetonitrile, dimethylformamide, water or the like or mixed solvents thereof are used as the solvent usually used in the reaction. Inorganic bases such as potassium carbonate or sodium carbonate, alkoxides such as tert-butoxypotassium or organic tertiary amines such as triethylamine or pyridine are used as such a base. A zerovalent palladium such as tetrakis(triphenylphosphine)palladium, a bivalent palladium such as palladium acetate or diphenylphosphinobutanepalladium dichloride or a bivalent nickel such as [bis (diphenylphosphino)ferrocene]nickel dichloride is used as the transition metal catalyst in an amount of 0.001 to 100 mol %. Furthermore, a tetra-$C_1$-$C_8$ alkylammonium halide or the like is used as a phase-transfer catalyst together in an amount of 0.001 to 100 mol %.

Among them, a combination of dimethylformamide as the solvent, potassium carbonate as the base and a zerovalent palladium such as tetrakis(triphenylphosphine)palladium as the transition metal catalyst, a combination of water as the solvent, potassium carbonate as the base, palladium acetate as the transition metal catalyst and tetrabutylammonium bromide as the phase-transfer catalyst, or a combination of a mixed solvent of toluene-methanol as the solvent, potassium carbonate as the base and palladium acetate as the transition metal catalyst, is preferred. The reaction is usually carried out at room temperature or under heating for 0.1 to 100 hours.

When X is shown by —$CH_2$—$Y^1$ described below in the cyanobiphenyl derivatives of the present invention, the cyanobiphenyl derivatives can be synthesized even according to, for example, the following reaction formula (e):

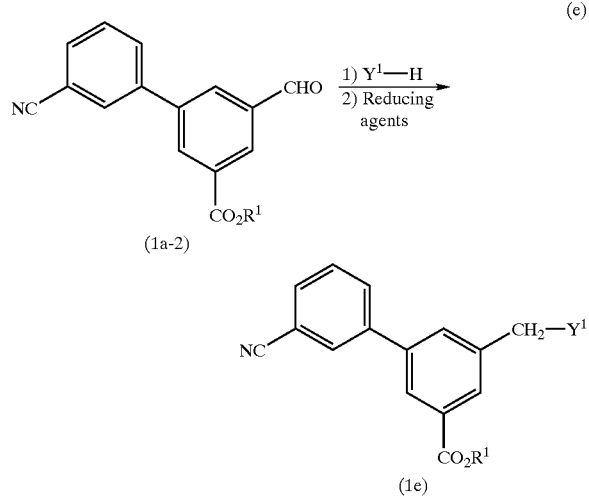

wherein $R^1$ is as defined in the formula (1), and $Y^1$ is as defined in the above formula (3).

That is, the cyanobiphenyl derivatives (1a-2) prepared according to the above reaction formula (a) are mixed with amines represented by $Y^1$—H, if necessary, in the presence of a catalytic amount of acids or dehydrating agents to produce imine intermediates which are subsequently reduced to produce the cyanobiphenyl derivatives (1e) which are the compounds of the present invention.

Ethers such as tetrahydrofuran, 1,4-dioxane or dimethoxyethane, hydrocarbons such as benzene or toluene, halogenated hydrocarbons such as dichloromethane or chloroform, alcohols such as methanol or ethanol, aprotic polar solvents such as dimethylformamide, acetonitrile, water and the like, or mixed solvents thereof are used as the solvent usually used in the reaction.

Toluene is preferred for the reaction for preparing the imine intermediates, and methanol is preferred for the subsequent reduction. Metal hydride complex compounds such as sodium borohydride or lithium aluminum hydride are used as the reducing agent. The reduction is also achieved by hydrogenation in the presence of transition metal catalysts such as palladium-carbon, platinum oxide or Raney nickel. Inorganic acids such as hydrochloric acid or sulfuric acid or organic acids such as benzenesulfonic acid or p-toluenesulfonic acid are used as the acid catalysts used in the preparation of the imine intermediates. Molecular sieves 4A, anhydrous sodium sulfate and the like are used as the dehydrating agents.

The reaction is usually carried out at room temperature or under heating for 1 to 100 hours. The reaction for preparing the imine intermediates is preferably carried out at 100 to 200° C., and the reduction is preferably carried out at room temperature.

When X is shown by —$CH_2$—$Y^4$ or —$CH_2$—$Y^1$ in the cyanobiphenyl derivatives of the present invention, the cyanobiphenyl derivatives can be synthesized according to, for example, the following reaction formula (f):

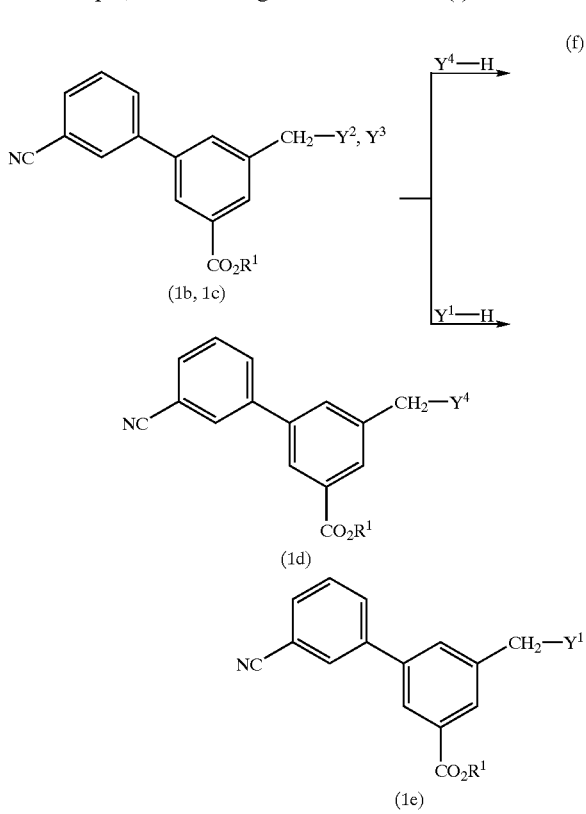

wherein $R^1$ is as defined in the formula (1), and $Y^2$, $Y^3$, $Y^4$ and $Y^1$ are each as defined in the above reaction formulae (b), (c), (d) and (e).

That is, the cyanobiphenyl derivatives (1b) or (1c) prepared according to the above reaction formula (b) or (c) are mixed with alcohols represented by $Y^4$—H in the presence of bases to thereby synthesize the cyanobiphenyl derivatives (1d) of the present invention. Furthermore, amines represented by $Y^1$—H are mixed therewith in the presence of bases to thereby synthesize the cyanobiphenyl derivatives (1e) of the present invention.

Ethers such as tetrahydrofuran or diethyl ether, hydrocarbons such as toluene or hexane, halogenated hydrocarbons such as dichloromethane or chloroform, aprotic polar solvents such as dimethylformamide, or mixed solvents thereof are used as the solvent usually used in the reaction. Metal hydrides such as sodium hydride, inorganic bases such as potassium carbonate or sodium carbonate or organic tertiary amines such as triethylamine or pyridine are used as such a base. The reaction is usually carried out at room temperature or under heating for 0.5 to 100 hours.

When X is shown by —$CH_2$—$N_3$ in the cyanobiphenyl derivatives of the present invention, the cyanobiphenyl derivatives can be synthesized even according to, for example, the following reaction formula (g):

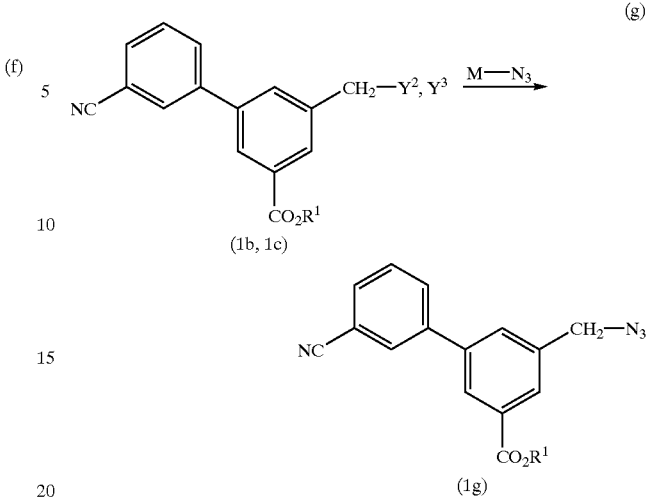

wherein $R^1$ is as defined in the formula (1), $Y^2$ and $Y^3$ are each as defined in the above (b) and (c) and M is an alkali metal atom such as lithium atom, sodium atom or potassium atom or a trialkylsilyl group.

That is, the cyanobiphenyl derivatives (1b) or (1c) prepared according to the above reaction formula (b) or (c) are mixed with azides represented by M—$N_3$ to thereby synthesize the cyanobiphenyl derivatives (1g) of the present invention.

Aprotic polar solvents such as dimethylformamide or hexamethylphosphoric triamide, ethers such as tetrahydrofuran or diethylene glycol dimethyl ether, halogenated hydrocarbons such as chloroform or dichloromethane, alcohols such as methanol or ethanol, water, or mixed solvents thereof are used as the solvent usually used in the reaction. Alkali metal azides such as sodium azide or potassium azide, trialkylsilyl azides and the like are used as the azides. A combination of dimethylformamide as the solvent with sodium azide as the azide is preferred.

When X is represented by —$CH_2$—$NH_2$ in the cyanobiphenyl derivatives of the present invention, the cyanobiphenyl derivatives can be synthesized even according to, for example, the following reaction formula (h):

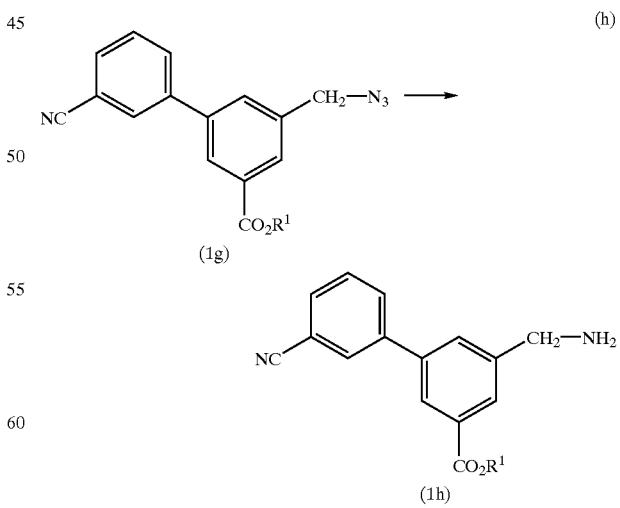

wherein $R^1$ is as defined as in the formula (1).

That is, the cyanobiphenyl derivatives (1g) prepared according to the above reaction formula (g) are reduced with suitable reducing agents to thereby synthesize the cyanobiphenyl derivatives (1h) of the present invention.

Aprotic polar solvents such as dimethylformamide or hexamethylphosphoric triamide, ethers such as tetrahydrofuran or diethylene glycol dimethyl ether, halogenated hydrocarbons such as chloroform or dichloromethane, alcohols such as methanol or ethanol and water are used as the solvent usually used in the reaction.

Metal hydride complexes such as sodium borohydride or lithium aluminum hydride, metal hydrides such as trialkyltin hydrides, a metal such as zinc or chromium or salts thereof are specifically used as the reducing agent. Otherwise, hydrogenation may be used in the presence of a catalyst such as palladium. A combination of methanol as the solvent with sodium borohydride as the reducing agent is preferred.

The cyanobiphenyl derivatives (1d) or (1e) of the present invention synthesized according to the above reaction formula (a), (d), (e) or () can be converted into the biphenylamidine derivatives described in WO99/26918 by carrying out an amidination as shown in the following reaction formula (i):

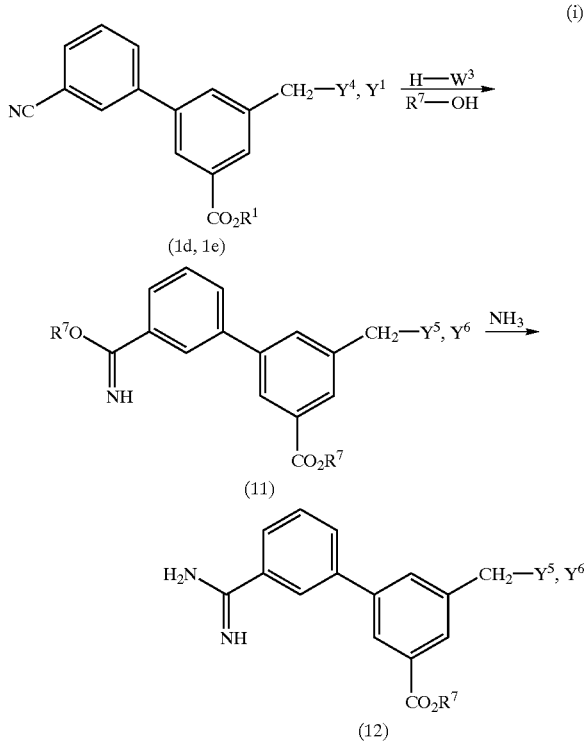

wherein $R^1$ is as defined in the formula (1), $Y^4$ and $Y^1$ are each as defined in the above reaction formulae (d) and (e), $R^7$ is a $C_1$-$C_4$ alkyl group, $Y^5$ is a group in which a nitrogen atom in the 4-piperidinomethyl group is unsubstituted or substituted with a $C_1$-$C_8$ alkyl group or a $C_1$-$C_8$ alkylcarbonyl group or an arylcarbonyl group in the above $Y^4$, $Y^6$ is a group in which a nitrogen atom in the 4-piperidinomethyl group is unsubstituted or substituted with a $C_1$-$C_8$ alkyl group, a $C_1$-$C_8$ alkylcarbonyl group or an arylcarbonyl group in the above $Y^1$, and $W^3$ is a chlorine atom, a bromine atom or an iodine atom.

The amidination is carried out under reaction conditions shown in the following (i-1) or (i-2).

(i-1) Amidination Through Imidate Intermediates Using a Solution of Hydrogen Halides in Alcohols The reaction is carried out by dissolving the cyanobiphenyl derivatives (1d) or (1e) of the present invention in alcohols represented by $R^7$—OH having 1 to 4 carbon atoms, which contain hydrogen halides represented by, for example, H—$W^3$ such as hydrogen chloride or hydrogen bromide. The reaction is usually carried out at $-20$ to $+30°$ C. for 12 to 96 hours and is preferably carried out in a solution of hydrogen chloride in methanol or ethanol at $-10$ to $+30°$ C. for 24 to 72 hours.

The reaction of the imidates (11) with ammonia proceeds by stirring the imidates (11) in alcohols having 1 to 4 carbon atoms such as methanol or ethanol, aliphatic ethers such as diethyl ether or halogenated hydrocarbons such as dichloromethane or chloroform or mixed solvents thereof containing the ammonia or amines such as hydroxylamines, hydrazines or carbamic acid esters to synthesize a biphenylamidine derivatives (12). The reaction is usually carried out at $-10$ to $+50°$ C. for 1 to 48 hours and is preferably carried out in methanol or ethanol at 0 to $30°$ C. for 2 to 12 hours.

(i-2) Amnidination Through Imidate Intermediates Prepared by While Directly Bubbling Hydrogen Halides The reaction proceeds by dissolving the cyanobiphenyl derivatives (1d) or (1e) of the present invention in ethers such as diethyl ether, halogenated hydrocarbons such as chloroform or aprotic solvents such as benzene, adding an equivalent amount or an excess of alcohols represented by $R^7$—OH having 1 to 4 carbon atoms, bubbling hydrogen halides represented by H—$W^3$ such as hydrogen chloride or hydrogen bromide under stirring at $-30$ to $0°$ C. for 30 minutes to 6 hours, then stopping the bubbling and more stirring the solution at 0 to $50°$ C. for 3 to 96 hours.

Preferably, the reaction is carried out by bubbling hydrogen chloride at $-10$ to $0°$ C. for 1 to 3 hours with stirring thereof in halogenated hydrocarbons containing an equivalent amount or an excess of methanol or ethanol and then stirring the solution at 10 to $40°$ C. for 8 to 24 hours without bubbling. The imidates (10) thus obtained can be converted into the biphenylamidine derivatives (12) by carrying out the stirring thereof in alcohols having 1 to 4 carbon atoms such as methanol or ethanol, aliphatic ethers such as diethyl ether or halogenated hydrocarbons such as chloroform or mixed solvents thereof which contain ammonia or amines such as hydroxylamine, hydrazine or carbamic acid esters. The reaction is usually carried out at $-20$ to $+50°$ C. for 1 to 48 hours and is preferably carried out in saturated ethanol solution of ammonia at 0 to $30°$ C. for 2 to 12 hours.

The compounds represented by the above formula (1) can respectively and mutually be synthesized by optional combination of other processes such as known oxidation, reduction, esterification or hydrolysis which are usually adoptable by those skilled in the art.

The cyanobiphenyl derivatives (1) synthesized as described above can be isolated and purified according to known methods, for example, extraction, precipitation, fractional chromatography, fractional crystallization or recrystallization. A salt of the compounds of the present invention can be synthesized by carrying out a usual salt-forming reaction.

The cyanobiphenyl derivatives of the present invention can effectively be used as synthetic intermediates for the biphenylamidine derivatives described in WO99/269 18.

EXAMPLES

The present invention will be illustrated using the following Productive Examples, Examples and Reference Examples. The scope of the present invention, however, is not restricted by the Productive Examples, Examples and Reference Examples.

Productive Example 1

Preparation of 3-cyanophenylboronic acid

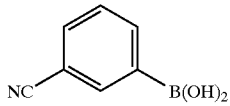

In 100 ml of anhydrous tetrahydrofuran, was dissolved 20 g of 3-bromobenzonitrile. To the resulting solution, was added 37.6 ml of triisopropoxyborane under a nitrogen atmosphere. The formed solution was cooled to −78° C., and 98.3 ml of a 1.6 M solution of n-butyllithium in hexane was dropped thereinto under stirring for about 30 minutes. After stirring the resulting mixture at room temperature for 30 minutes, the mixture was then cooled to 0° C., and 220 ml of a 4 M sulfuric acid was added. The prepared solution was refluxed overnight and subsequently recooled to 0C. To the cooled solution, was added 340 ml of a 5 M aqueous solution of sodium hydroxide. The resulting solution was extracted with 200 ml of diethyl ether, and an aqueous layer was separated. To the aqueous layer, was added a 6 M hydrochloric acid until pH attained 2. The resulting mixture was extracted with 300 ml of ethyl acetate twice. The extract was dried over magnesium sulfate, and the solvent was then evaporated. The resulting crude product was recrystallized from dimethylformamide-water to provide 11.6 g (72%) of the title compound as a needlelike light-yellow crystal.

$^1$H-NMR (270 MHz, DMSO-d6): δ 7.6–8.3 (m, 4H), 8.5 (brs, 2H).

Productive Example 2

Preparation of methyl 3-bromo-5-(hydroxymethyl)benzoate

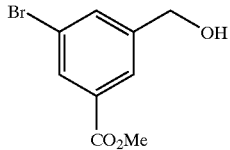

In 25 ml of tetrahydrofuran, was dissolved 10.00 g of dimethyl 3-bromoisophthalate. 1.66 g of sodium borohydride was added to the above solution and thereby a suspension was obtained. A mixed solution of 7.4 ml of methanol and 25 ml of tetrahydrofuran was slowly dropped into the resulting suspension. After completing the dropping, the reaction solution was refluxed for 30 minutes. A 1 M hydrochloric acid was added to the solution to quench the reaction. The resulting solution was extracted with ethyl acetate, and the organic layer was dried over magnesium sulfate. The solvent was removed under reduced pressure to afford 9.30 g of the title compound as a colorless oil quantitatively.

$^1$H-NMR (270 MHz, CDCl$_3$): δ 53.9 (s, 3H), 4.73 (d, 2H, J=5.4 Hz), 7.7–8.1 (m, 3H).

Example 1

Synthesis of methyl 3-(3-cyanophenyl)-5-(hydroxymethyl)benzoate

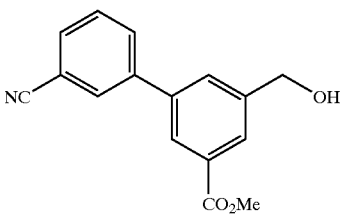

In 50 ml of anhydrous dimethylformamide, was dissolved 3.08 g of the compound obtained in Productive Example 2. To the resulting solution, were added 2.32 of the compound obtained in Productive Example 1, 2.18 g of potassium carbonate and 456 mg of tetrakis(triphenylphosphine) palladium. The prepared mixture was stirred at 90° C. under heating overnight. Water was added to quench the reaction, and the resulting solution was extracted with ethyl acetate. The obtained extract was dried over magnesium sulfate, and the solvent was evaporated. The obtained crude product was purified by silica gel column chromatography to provide 2.05 g (73%) of the title compound as a white crystal.

$^1$H-NMR (270 MHZ, CDCl$_3$): δ 2.1 (brs, 1H), 3.96 (s, H), 4.84 (d, 2H, J=3.7 Hz), 7.5–8.2 (m, 7H).

Example 2

Synthesis of methyl 3-(3-cyanophenyl)-5-(hydroxymethyl)benzoate

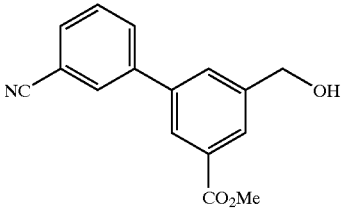

In 35 ml of ion exchange water, were dissolved 6.31 g of the compound obtained in Productive Example 1, 10.01 g of the compound obtained in Productive Example 2, 13.23 g of tetrabutylammonium bromide, 14.02 g of potassium carbonate and 0.021 g of palladium acetate under a nitrogen stream. The resulting solution was stirred under heating at 60° C. for 40 minutes. The reaction solution was extracted with ethyl acetate, and the organic layer was washed with saturated brine and then dried over sodium sulfate. The solvent was evaporated. The obtained crude product was purified by silica gel column chromatography to afford 8.58 g (79%) of the title compound as a white crystal.

$^1$H-NMR (270 MHz, CDCl$_3$): δ 2.1 (brs, 1H), 3.96 (s, 3H), 4.84 (d, 2H, J=3.7 Hz), 7.5–8.2 (m, 7H).

Example 3

Synthesis of methyl 3-(3-cyanophenyl)-5-(hydroxymethyl)benzoate

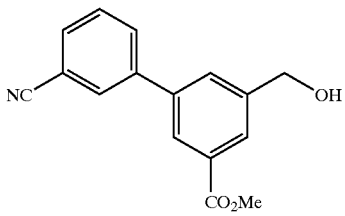

To a mixed solvent of 1260 ml of toluene with 290 ml of methanol, were added 140 g of the compound obtained in Productive Example 1 and 88 g of the compound obtained in Productive Example 2. To the resulting mixture, were further added 0.95 g of palladium acetate and 648 g of a 25% aqueous solution of potassium carbonate. The obtained mixture was stirred under heating at 55° C. for 2 hours. The resulting reaction mixture was filtered and separated, and the aqueous layer was extracted with 300 ml of toluene. Organic layers were combined, washed with a dilute hydrochloric acid, dried and then concentrated. The obtained crude product was purified by silica gel column chromatography to provide 90 g (94%) of the title compound as a white crystal.

$^1$H-NMR (270 MHz, CDCl$_3$): δ 2.1 (brs, 1H), 3.96 (s, 3H), 4.84 (d, 2H, J=3.7 Hz), 7.5–8.2 (m, 7H).

The following compound of Example 4 was synthesized according to the same method as that in Example 2 or 3:

Example 4

Synthesis of dimethyl 3-(3-cyanophenyl)-isophthalate

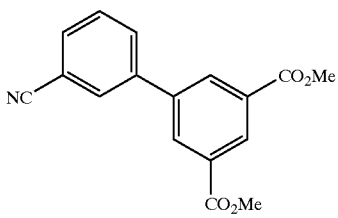

$^1$H-NMR (270 MHz, CDCl$_3$): δ 4.00 (s, 6H), 7.5–8.0 (m, 4H), 8.44 (s, 2H), 8.72 (s, 1H).

Example 5

Synthesis of methyl 3-(3-cyanophenyl)-5-(bromomethyl)benzoate

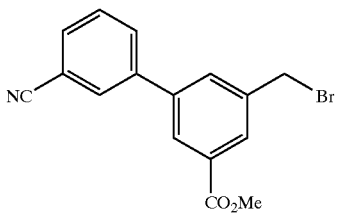

To 20 ml of diethyl ether, was added 1.0 g of the compound obtained in Example 1, 2 or 3. Into the prepared suspension, was slowly dropped 0.5 ml of phosphorus tiibromide. The resulting solution was stirred at room temperature for 19 hours. Water was added to the reaction solution to quench the reaction, and the reaction mixture was extracted with ethyl acetate. The organic layer was washed with saturated brine and dried over sodium sulfate. The solvent was then removed under reduced pressure to afford 1.2 g (98%) of the title compound as a light-yellow crystal.

$^1$H-NMR (270 MHz, CDCl$_3$): δ 3.97 (s, 3H), 4.58 (s, 2H), 7.5–7.9 (m, 5H), 8.1–8.2 (m, 2H).

Example 6

Synthesis of methyl 3-(3-cyanophenyl)-5-[((N-t-butoxycarbonyl)piperidin-4-ylmethyl)aminomethyl]benzoate

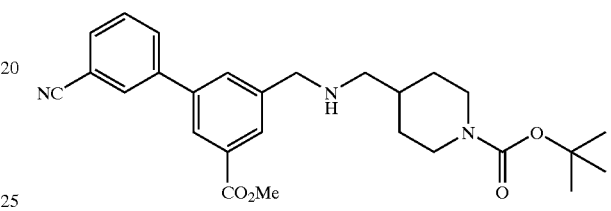

In 150 ml of anhydrous tetrahydrofuran, was dissolved 5.5 g of the compound obtained in Example 5. To the resulting solution, was added 7.92 g of 4-aminomethyl-(N-t-butoxycarbonyl)piperidine. The obtained mixture was stirred at room temperature overnight. The resulting reaction solution was poured into a 0.5 M aqueous solution of potassium hydrogensulfate to quench the reaction. The reaction solution was extracted with ethyl acetate and dried over sodium sulfate, and the solvent was then evaporated to provide 10 g (as a potassium hydrogensulfate salt, quantitatively) of the title compound.

1H-NMR (270 MHz, CDCl$_3$): δ 1.0–1.3 (m, 2H), 1.43 (s, 9H), 1.7–2.0 (m, 3H), 2.6–2.8 (m, 4H), 3.95 (s, 3H), 4.0–4.2 (brs, 4H), 7.5–7.7 (m, 2H), 7.9–8.0 (m, 2H), 8.20 (s, 2H).

The compounds of Examples 7 to 8 described below were synthesized according to the same method as that in Example 6, with the proviso that sodium hydride was used as a base.

Example 7

Synthesis of methyl 3-(3-cyanophenyl)-5-[((N-t-butoxycarbonyl)piperidin-4-yl)methoxymethyl]benzoate

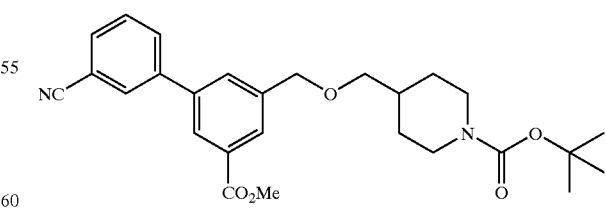

$^1$H-NMR (270 MHz, CDCl$_3$): δ 1.0–1.3 (m, 2H), 1.45 (s, 9H), 1.5–1.6 (m, 1H), 1.6–1.9 (m, 2H), 2.71 (t, 2H, J=12.2 Hz), 3.38 (d, 2H, J=5.9 Hz), 3.97 (s, 3H), 4.0–4.2 (m, 2H), 4.60 (s, 2H), 7.5–7.9 (m, 4H), 7.90 (s, 1H), 8.03 (s, 1H), 8.16 (s, 1H).

Example 8

Synthesis of methyl 3-(3-cyanophenyl)-5-[(N-isopropylpiperidin-4-yl)methoxymethyl]benzoate

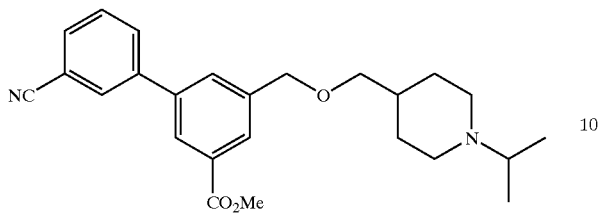

¹H-NMR (270 MHz, CDCl₃): δ 1.04 (d, 6H, J=6.6 Hz), 1.6–1.9 (m, 4H), 2.13 (dt, 2H, J=11.6 Hz, 2.3 Hz), 2.70 (quint, 1H, J=6.6 Hz), 2.90 (d, 2H, J=11.6 Hz), 3.38 (d, 2H, J=6.6 Hz), 3.96 (s, 3H), 4.60 (s, 2H), 7.5–7.7 (m, 2H), 7.74 (s, 1H), 7.8–7.9 (m, 1H), 8.03 (s, 1H), 8.15 (s, 1H).

Example 9

Synthesis of methyl 3-(3-cyanophenyl)-5-(azidomethyl)benzoate

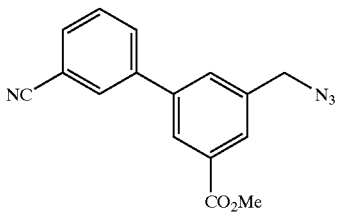

In 33 ml of dimethylformamide, was dissolved 1.1 g of the compound obtained in Example 5. To the resulting solution, was slowly added 325 mg of sodium azide. The obtained reaction solution was stirred at room temperature for 2 hours, and 80 ml of water and 120 ml of ethyl acetate were then added thereto to extract organic substances. The aqueous layer was extracted with 100 ml of ethyl acetate twice. The resulting extract was washed with saturated brine and dried with anhydrous sodium sulfate. The solvent was removed under reduced pressure to afford 925 mg (95%) of the title compound as a light-yellow oil.

GC-MS (M−N₂)=264.

Example 10

Synthesis of methyl 3-(3-cyanophenyl)-5-(aminomethyl)benzoate

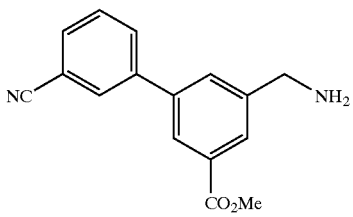

The compound obtained in Example 9 was dissolved in 66 ml of ethanol. To the resulting solution, was added 1.1 g of palladium-barium carbonate. The interior of the flask was then replaced with hydrogen. The solution was stirred at room temperature for 6 hours, and then the catalyst was filtered through Celite. The resulting filtrate was concentrated and then purified by silica gel column chromatography to provide 794 mg (94%) of the title compound.

GC-MS (M−H)=265.

Example 11

Synthesis of methyl 3-(3-cyanophenyl)-5-(formyl)benzoate

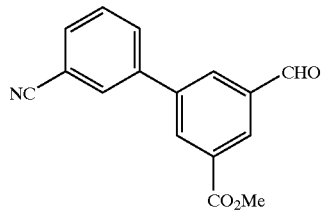

In 200 ml of dichloromethane, was dissolved 9.05 g of the compound obtained in Example 1, 2 or 3. To the resulting solution, was added 20.6 g of manganese dioxide. The obtained mixture was stirred at room temperature for 40 hours. The reaction solution was filtered through Celite, and the Celite was further washed with dichloromethane. Each filtrate was combined into one portion, and the solvent was removed under reduced pressure to afford 7.65 g (85%) of the title compound as a white crystal.

¹H-NMR (270 MHz, CDCl₃): δ 4.02 (s, 3H), 7.5–8.7 (m, 7H), 10.16 (s, 1H).

Example 12

Synthesis of methyl 3-(3-cyanophenyl)-5-(dimethoxymethyl)benzoate

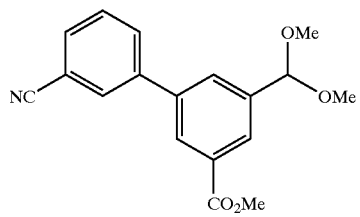

In 200 ml of methanol, were dissolved 2.00 g of the compound obtained in Example 11, 0.86 ml of methyl orthoformate and 0.004 g of p-toluenesulfonic acid monohydrate. The resulting solution was refluxed for 12 hours. After completing the reaction, 0.03 ml of triethylamine was added to the reaction solution, and the solvent was then removed under reduced pressure. Ethyl acetate was added to the residue, and the resulting solution was extracted with ethyl acetate. The organic layer was dried over sodium sulfate. The solvent was removed under reduced pressure to provide 2.35 g (quantitatively) of the title compound.

¹H-NMR (270 MHz, CDCl₃): δ 3.35 (s, 6H), 3.90 (s, 3H), 5.85 (s, 1H), 7.5–8.7 (m, 7H); GC-MS (M+H)=312.

Example 13

Synthesis of methyl 3-(3-cyanophenyl)-5-(dibromomethyl)benzoate

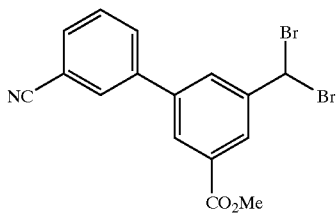

In 10 ml of dichloromethane, was dissolved 6.2 g of triphenyl phosphite. The resulting solution was cooled to 0° C., and then 3.2 g of bromine was slowly dropped. The reaction solution was cooled to −15° C., and 5 ml of a solution of 2.65 g of the compound obtained in Example 11 in dichloromethane was slowly dropped therein. After completing the dropping, the temperature was returned to room temperature, and subsequently the reaction solution was filtered through basic alumina. The solvent was removed under reduced pressure. The resulting residue was purified by silica gel column chromatography to afford 3.48 g (85%) of the title compound.

$^1$H-NMR (270 MHz, CDCl$_3$): δ 4.02 (s, 3H), 6.80 (s, 1H), 7.5–8.7 (m, 7H); GC-MS (M+H)=408.

Example 14

Synthesis of methyl 3-(3-cyanophenyl)-5-[(piperidin-4-ylmethyl)aminomethyl]benzoate

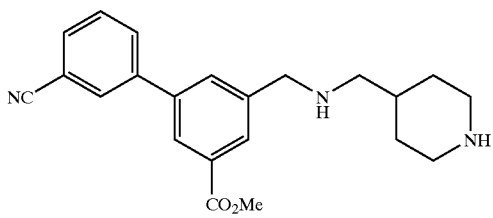

In 30 ml of toluene, were dissolved 3.00 g of the compound obtained in Example 11 and 1.50 g of 4-aminomethylpiperidine. The resulting solution was refluxed for 3 hours to remove the produced water. The solvent was evaporated from the reaction solution under reduced pressure, and 10 ml of tetrahydrofuran and 20 ml of methanol were added to the residue to provide a solution. To the resulting solution, was added 0.500 g of sodium borohydride under cooling with ice. The mixture was stirred at this temperature for 1 hour, then returned to room temperature and stirred for another hour. To the resulting solution was added a 1 M hydrochloric acid to quench the reaction. The resulting solution was washed with ethyl acetate. A 1 M aqueous solution of sodium hydroxide was added to the obtained aqueous layer until the pH attained 10. The resulting solution was extracted with ethyl acetate. The resulting organic layer was washed with saturated brine and subsequently dried over sodium sulfate, and the solvent was removed under reduced pressure to provide 2.9 g (71%) of the title compound as an oil.

$^1$H-NMR (270 MHz, CDCl$_3$): δ 1.0–3.5 (m, 11H), 3.90 (s, 2H), 3.96 (s, 3H), 7.5–8.5 (m, 7H).

Example 15

Synthesis of methyl 3-(3-cyanophenyl)-5-[(piperidin-4-ylmethyl)aminomethyl]benzoate

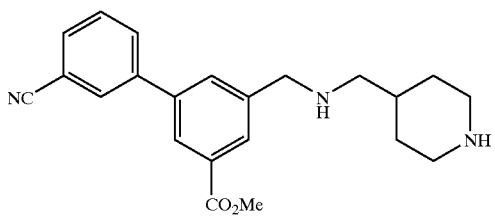

In 20 ml of toluene, were added 1.0 g of the compound obtained in Example 11 and 500 mg of 4-aminomethylpiperidine. The resulting mixture was refluxed using a Dean-Stark device under heating for 2 hours to remove the produced water. The solvent was then evaporated, and 20 ml of anhydrous methanol was added to dissolve the residue. To the obtained solution, was added 100 mg of 5% palladium-carbon. The mixture was stirred at room temperature under hydrogen atmosphere. After 4 hours, 200 mg of the 5% palladium-carbon was further added, and the reaction mixture was stirred for another 65 hours. The catalyst was separated by filtration, and the reaction mixture was concentrated. The resulting concentrate was then dissolved in a mixed solvent of water-dichloromethane, and the aqueous layer was separated and concentrated to afford 0.82 g (60%) of the title compound as a light-yellow oily substance.

$^1$H-NMR (270 MHz, CDCl$_3$): δ 1.0–3.5 (m, 11H), 3.90 (s, 2H), 3.96 (s, 3H), 7.5–8.5 (m, 7H).

Example 16

Synthesis of methyl 3-(3-cyanophenyl)-5-[(piperidin-4-yl)methoxymethyl]benzoate

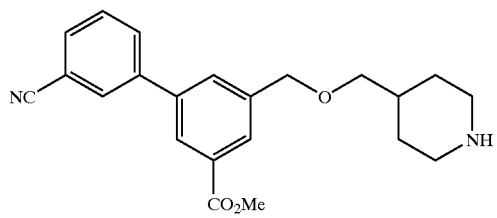

In 20 ml of methanol, was dissolved 400 mg of the compound obtained in Example 7. To the resulting solution, was added 20 ml of a 2 M hydrochloric acid under cooling with ice and stirring. After stirring at 0° C. to room temperature for 7 hours, the resulting solution was then concentrated to provide 298 mg (95%) of the title compound.

$^1$H-NMR (270 MHz, CDCl$_3$): δ 1.0–3.4 (m, 11H), 3.97 (s, 3H), 4.05 (s, 2H), 7.5–8.5 (m, 7 H).

Example 17

Synthesis of methyl 3-(3-cyanophenyl)-5-[(1-acetylpiperidin-4-yl)methoxymethyl]benzoate

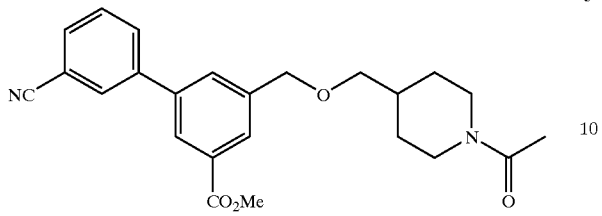

In 20 ml of dichloromethane, was dissolved 298 mg of the compound obtained in Example 16. To the resulting solution, was added 3.0 ml of triethylamine. To the obtained mixture, 0.46 ml of acetyl chloride was added under cooling with ice and stirring. The mixture was stirred at 0° C. to room temperature for 18 hours. The obtained mixture was poured into a saturated aqueous solution of sodium hydrogensulfate and extracted with ethyl acetate. The organic layer was washed with a saturated aqueous solution of sodium hydrogencarbonate and saturated brine and subsequently dried over magnesium sulfate. The solvent was removed under reduced pressure, and the obtained crude product was purified by silica gel column chromatography to afford 260 mg (78%) of the title compound.

$^1$H-NMR (270 MHz, CDCl$_3$): δ 1.0–1.3 (m,2H), 1.7–2.0 (m, 3H), 2.09 (s, 3H), 2.56 (td, 1H, J=12.8, 2.9 Hz), 3.06 (td, 1H, J=13.2, 2.0 Hz), 3.2–3.5 (m, 2H), 3.83 (brd, 1H, J=13.5 Hz), 3.97(s, 3H), 4.65 (s, 2H), 4.5–4.8 (m, 1H), 7.58 (t, 1H, J=7.8 Hz), 7.6–7.8 (m, 1H), 7.72 (s, 1H), 7.85 (d, 1H, J=7.9 Hz), 7.90 (s, 1H), 8.03 (s, 1H), 8.17(s, 1H).

Example 18

Synthesis of methyl 3-(3-cyanophenyl)-5-[2-(N-t-butoxycarbonylpiperidin-4-yl)methoxymethyl]benzoate

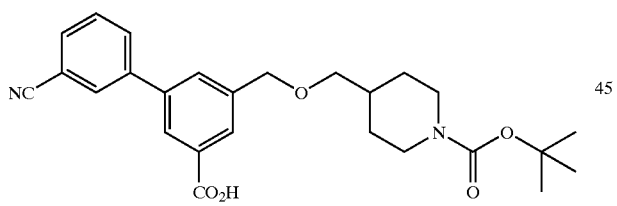

In 20 ml of methanol, was dissolved 1.43 g of the compound obtained in Example 7. To the resulting solution, was added 2 ml of water. To the prepared mixture, was added 1.54 ml of a 4 M aqueous solution of lithium hydroxide. The obtained mixture was stirred at room temperature for 3 hours. A saturated aqueous solution of ammonium chloride was added to acidify the mixture. The acidified mixture was then extracted with ethyl acetate. The organic layer was washed with saturated brine and dried over magnesium sulfate. The solvent was evaporated, and the obtained crude product was purified by silica gel column chromatography to provide 1.03 g (74%) of the title compound.

$^1$H-NMR (270 MHz, CDCl$_3$): δ 1.0–1.3 (m, 2H), 1.46 (s, 9H), 1.7–2.0 (m, 3H), 2.56 (td, 1H, J=12.8, 2.9 Hz), 3.05 (td, 1H, J=13.2, 2.0 Hz), 3.2–3.5 (m, 2H), 3.83 (brd, 1H, J=13.5 Hz), 4.65 (s, 2H), 4.6–4.8 (m, 1H), 7.60 (t, 1H, J=7.8 Hz), 7.6–7.8 (m, 1H), 7.74 (s, 1H), 7.85 (d, 1H, J=7.9 Hz), 7.90 (s, 1H), 8.03 (s, 1H), 8.16 (s, 1H).

Reference Example 1

Synthesis of methyl 3-(3-amidinophenyl)-5-[((4-piperidinylmethyl)amino)methyl]-5-benzoate

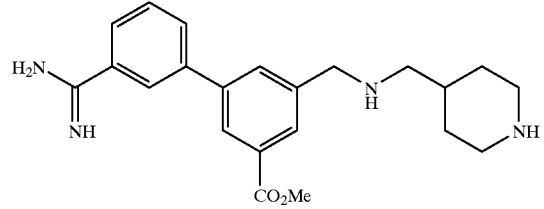

In 60 ml of dichloromethane, was dissolved 6.0 g of the compound obtained in Example 6. To the resulting solution, was added 3.0 ml of methanol. Gaseous hydrogen chloride was bubbled into the solution with stirring under cooling with ice for 30 minutes. After stirring the solution at 0° C. for 30 minutes and at room temperature for 20 hours, the resulting solution was concentrated. To the residue, was added 30 ml of a saturated ammonia-ethanol solution, and the resulting solution was stirred at room temperature for 5 hours and then concentrated. The obtained crude product was purified by using HP-20 column chromatography (30 g, eluting solvent: water-methanol) to afford 4.89 g (99%) of the title compound.

$^1$H-NMR (270 MHz, DMSO-d$_6$+D$_2$O): δ 1.3–1.5 (m, 2H), 1.96–2.00 (m, 2H), 2.1 (brs, 1H), 2.7–3.0 (m, 4H), 3.97 (s, 3H), 4.32 (s, 2H), 7.76 (t, 1H, J=7.8 Hz), 7.89 (d, 1H, J=7.8 Hz), 8.1–8.5 (m, 5H).

The following compounds of Reference Examples 2 to 5 were synthesized according to the same method as that in Reference Example 1.

Reference Example 2

Synthesis of methyl 3-(3-amidinophenyl)-5-[((4-piperidinylmethyl)amino)methyl]-5-benzoate

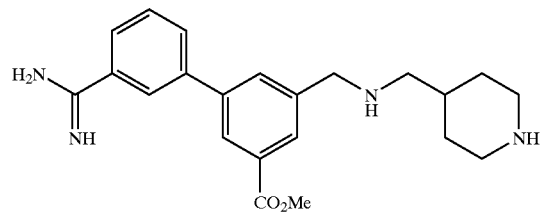

The compound obtained in Example 14 or 15 was used as a starting material to provide the title compound. (The spectral data were the same as those in Reference Example 1.)

Reference Example 3

Synthesis of methyl 3-(3-amidinophenyl)-5-[(4-piperidinyl)methoxymethyl]-5-benzoate

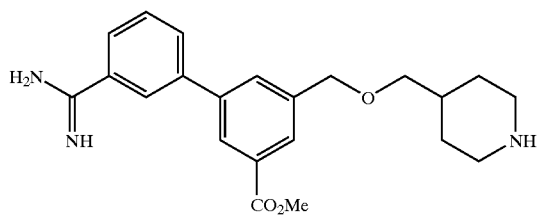

$^1$H-NMR (270 MHz, DMSO-d$_6$): δ 1.3–1.5 (m, 2H), 1.7–2.0 (m, 3H), 2.7–2.9 (m, 2H), 3.15–3.3 (m, 2H), 3.38 (d, 2H, J=6.3 Hz), 3.91 (s, 3H), 4.64 (s, 2H), 7.69 (t, 1H, J=7.9 Hz), 7.86 (d, 1H, J=7.9 Hz), 7.99 (s, 1H), 8.02 (s, 1H), 8.07 (d, 1H, J=7.6 Hz), 8.15 (s, 1H), 8.28 (s, 1H), 8.55–8.85 (brs, 1H), 9.19–9.52 (s, 2H).

Reference Example 4

Synthesis of methyl 3-(3-amidinophenyl)-5-[(N-isopropyl-4-piperidinyl)methoxymethyl]-5-benzoate

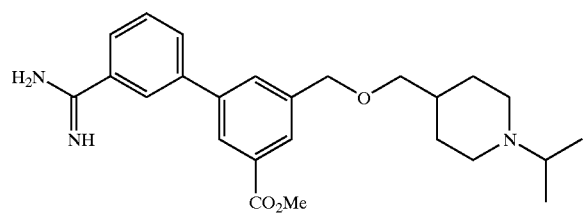

$^1$H-NMR (270 MHz, DMSO-d$_6$): δ 1.26 (d, 6H, J=6.9 Hz), 1.6–2.0 (m, 5H), 2.8–3.0 (m, 2H), 3.1–3.5 (m, 5H), 3.92 (s, 3H), 4.65 (s, 2H), 7.74 (t, 1H, J=7.8 Hz), 7.90 (d, 1H, J=7.9 Hz), 7.98 (s, 1H), 8.07 (s, 1H), 8.07 (d, 1H, J=7.6 Hz), 8.08 (d, 1H, J=8.3 Hz), 8.18 (s, 1H), 8.27 (s, 1H), 9.40–9.62 (brs, 3H).

Reference Example 5

Synthesis of methyl 3-(3-amidinophenyl)-5-[(N-acetylpiperidin-4-yl)methoxymethyl]-5-benzoate

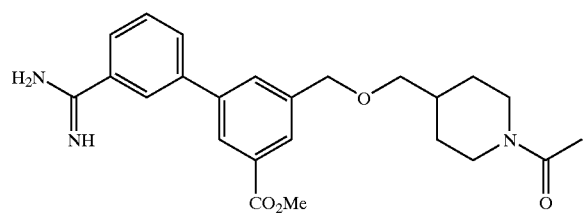

$^1$H-NMR (270 MHz, DMSO-d$_6$): δ 0.9–1.3 (m, 2H), 1.6–2.0 (m, 3H), 1.97 (s, 3H), 2.4–2.65 (m, 1H), 3.00 (brt, 1H, J=11.7 Hz), 3.2–3.5 (m, 2H), 3.80 (brd, 1H, J=14.9 Hz), 3.91 (s, 3H), 4.37 (brd, 1H, J=4.4 Hz), 4.63 (s, 2H), 7.71 (t, 1H, J=7.7 Hz), 7.83 (d, 1H, J=7.9 Hz), 7.98 (s, 2H), 8.02 (d, 1H, J=7.9 Hz), 8.11 (s, 1H), 8.17 (s, 1H), 8.25 (s, 1H), 9.40–10.0 (br, 3H).

Reference Example 6

Synthesis of methyl 3-(3-amidinophenyl)-5-[(((N-acetimidoylpiperidin-4-yl)methyl)amino)methyl]benzoate

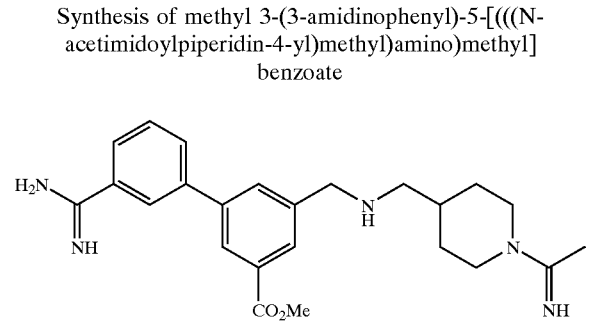

To 4.79 g of the compound obtained in Reference Example 1 or 2 and 3.10 g of ethyl acetimidate monohydrochloride, were added 50 ml of ethanol. To the resulting solution, was dropped 5.25 ml of triethylamine with stirring under cooling with ice. The resulting mixture was warmed up from 0° C. to room temperature, stirred for 36 hours and then concentrated. The obtained crude product was purified by HPLC (ODS, eluent: water-methanol) to afford 4.37 g (82%) of the title compound.

$^1$H-NMR (270 MHz, DMSO-d$_6$+D$_2$O): δ 1.2–1.5 (m, 2H), 1.8–2.0 (m, 2H), 2.1 (brs, 1H), 2.26 (s, 3H), 2.9–3.2 (m, 4H), 3.94 (s, 3H), 3.9–4.1 (m, 2H), 4.35 (s, 2H), 7.8–8.2 (m, 6H), 8.43 (s, 1H).

The following compound of Reference Example 7 was synthesized according to the same reaction as that in Reference Example 6.

Reference Example 7

Synthesis of methyl 3-(3-amidinophenyl)-5-[(1-acetimidoyl-4-piperidinyl)methoxymethyl]benzoate

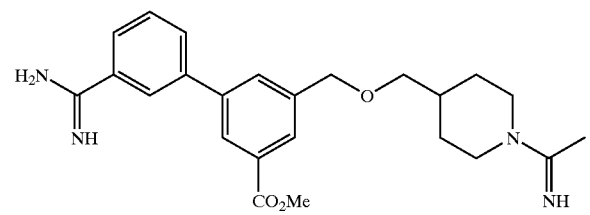

$^1$H-NMR (270 MHz, DMSO-d$_6$): δ 1.1–1.4 (m, 2H), 1.7–2.1 (m, 3H), 2.50 (s, 3H), 3.0–3.5 (m, 4H), 3.8–4.0 (m, 1H), 3.91 (s, 3H), 4.0–4.2 (m, 1H), 4.64 (s, 2H), 7.74 (t, 1H, J=7.8 Hz), 7.87 (d, 1H, J=7.6 Hz), 8.00 (s, 1H), 8.03 (s, 1H), 8.07 (d, 1H, J=7.6 Hz), 8.16 (s, 1H), 8.28 (s, 1H), 8.64–9.20 (brs, 1H), 9.25–9.54 (brs, 2H).

Reference Example 8

Synthesis of methyl 3-(3-amidinophenyl)-5-[(((N-acetimidoylpiperidin-4-yl)methyl)amino)methyl]benzoate

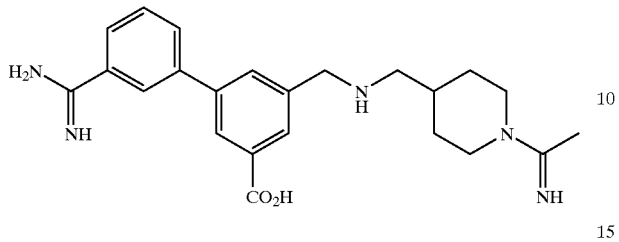

In 27 ml of a 2 M hydrochloric acid, was dissolved 2.71 g of the compound in Reference Example 6. The resulting solution was stirred at 70° C. for 24 hours and then concentrated. The obtained crude product was purified by HPLC (ODS, eluent: water-methanol) to provide the title compound (2.00 g, yield: 76%).

$^1$H-NMR(270 MHz, DMSO-$d_6$): δ 1.2–1.5 (m, 2H), 1.9–2.0 (m, 2H), 2.28 (s, 3H), 2.1–2.3 (m, 1H), 2.9–3.4 (m, 4H), 4.02 (dd, 2H, J=5.3 Hz, 13.5 Hz), 4.34 (s, 2H), 7.7–8.0 (m, 2H), 8.1–8.3 (m, 3H), 8.41 (s, 1H), 8.47 (s, 1H).

The following compounds of Reference Examples 9 to 11 were synthesized according to the same reaction as that in Reference Example 8.

Reference Example 9

Synthesis of methyl 3-(3-amidinophenyl)-5-[(N-acetimidoyl-4-piperidinyl)methoxymethyl]benzoate

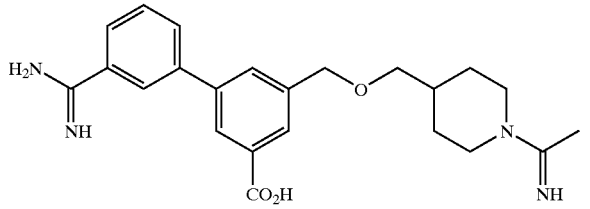

$^1$H-NMR (270 MHz, DMSO-$d_6$): δ 1.2–1.6 (m, 2H), 1.9–2.2 (m, 3H), 2.31 (s, 3H), 3.0–3.4 (m, 2H), 3.47 (d, 2H, J=5.9 Hz), 3.9–4.1 (m, 2H), 4.65 (s, 2H), 7.6–7.8 (m, 3H), 8.0–8.1 (m, 2H), 8.10 (s, 1H), 8.24 (s, 1H).

Reference Example 10

Synthesis of methyl 3-(3-amidinophenyl)-5-[(N-isopropylpiperidin-4-yl)methoxymethyl]benzoate

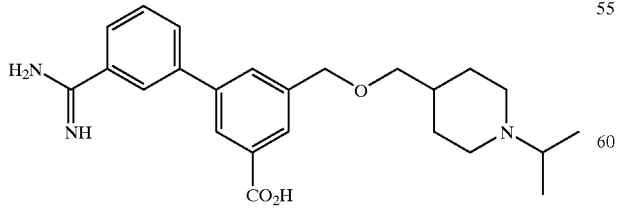

$^1$H-NMR (270 MHz, DMSO-$d_6$): δ 1.18 (d, 6H, J=6.6 Hz), 1.4–1.65 (m, 2H), 1.75–1.95 (m, 3H), 2.6–2.9 (m, 2H), 3.1–3.5 (m, 5H), 4.33 (m, 2H), 4.62 (s, 2H), 7.73 (t, 1H, J=7.9 Hz), 7.84 (d, 1H, J=7.6 Hz), 7.94 (s, 1H), 7.97 (s, 1H), 8.06 (d, 1H, J=7.6 Hz), 8.18 (s, 1H), 8.27 (s, 1H), 9.45 (brs, 3H).

Reference Example 11

Synthesis of methyl 3-(3-amidinophenyl)-5-[((4-piperidinylmethyl)amino)methyl]benzoate

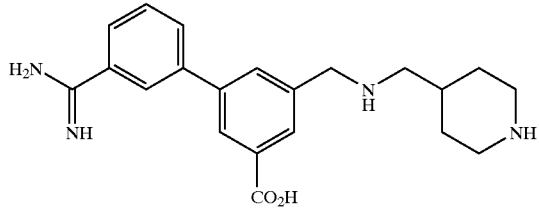

$^1$H-NMR (270 MHz, DMSO-$d_6$+$D_2O$): δ 1.3–1.5. (m, 2H), 1.96 (d, 2H, J=14 Hz), 2.11 (brs, 1H), 2.7–3.0 (m, 4H), 4.30 (s, 2H), 7.74 (t, 1H, J=7.7 Hz), 8.1–8.5 (m, 5H).

Reference Example 12

Determination of Inhibitory Activity of Activated Blood Coagulation Factor X (FXa)

A test substance was dissolved in water or water containing organic solvents (DMSO, ethanol or methanol) at a suitable concentration to provide a specimen. To 70 μl each of the resulting specimens serially diluted with water, were added 90 μl of a 100 mM Tris buffer (pH 8.4), 20 μl of a 50 mM Tris buffer (pH 8.4) containing 50 mU/ml human FXa and 2 mM of a substrate (S-2765 manufactured by Daiichi Pure Chemicals Co., Ltd.). Incubation was carried out for 30 minutes. To the incubated mixture, was then added 50 μl of a 50% acetic acid. The absorbance ($A_{405}$) was determined. A mixture prepared by adding the Tris buffer instead of the FXa was used as a blank, and a mixture containing water instead of the specimen was used as a control. The 50% inhibitory activity ($IC_{50}$) was determined as the indication of FXa inhibitory activity.

As a result, the inhibitory activity of $IC_{50}$=0.01 to 0.1 μM was found in the compounds of Reference Examples 6, 7 and 9, and the inhibition activity of $IC_{50}$=0.1 to 1 μM was found in the compounds of Reference Examples 3, 4, 5, 8 and 10.

Industrial Applicability

The cyanobiphenyl derivatives of the present invention can be used as useful intermediates for biphenylamidine derivatives used as inhibitors of FXa.

What is claimed is:

1. A cyanobiphenyl compound represented by the following formula (1):

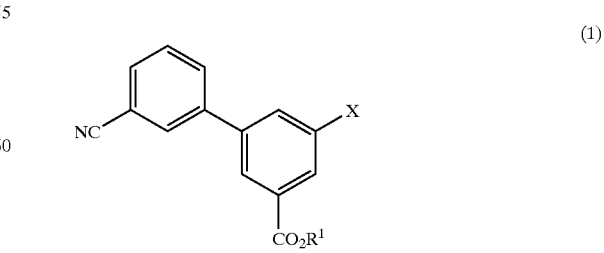

wherein $R^1$ is a hydrogen atom, a $C_1$–$C_8$ alkyl group, an aryl group or an aralkyl group; X is a carboxyl group, a $C_1$–$C_8$ alkoxycarbonyl group, an aryloxycarbonyl group, an aralkoxycarbonyl group, a formyl group, the formula:

wherein Y is a chlorine atom, a bromine atom, an iodine atom, an azide group, —OR² wherein R² is a hydrogen atom, a $C_1$–$C_8$ alkylsulfonyl group optionally substituted with more halogen atoms, an arylsulfonyl group or 4-piperidinomethyl group wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group, or —NHR³ wherein R³ is a hydrogen atom or a 4-piperidinomethyl group and wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group, the formula:

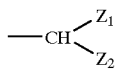

wherein $Z_1$ and $Z_2$ are each independently a chlorine atom, a bromine atom or an iodine atom, or the formula:

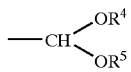

wherein R⁴ and R⁵ are each independently a hydrogen atom, a $C_1$–$C_8$ alkyl group or a $C_1$–$C_8$ alkylcarbonyl group or both together may form a ring when R⁴ and R⁵ are each a $C_1$–$C_8$ alkyl group, or its salts thereof.

2. The cyanobiphenyl compound or its salts thereof according to claim 1, wherein, in formula (1), R¹ is a hydrogen atom or a $C_1$–$C_8$ alkyl group; X is a $C_1$–$C_8$ alkoxycarbonyl group, a formyl group, the formula:

wherein Y is a chlorine atom, a bromine atom, an iodine atom, an azide group, —OR² wherein R² is a hydrogen atom or 4-piperidinomethyl group wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group, or —NHR³ wherein R³ is a hydrogen atom or a 4-piperidinomethyl group and wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group, the formula:

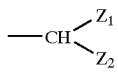

wherein $Z_1$ and $Z_2$ are each independently a chlorine atom, a bromine atom or an iodine atom, or the formula:

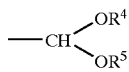

wherein R⁴ and R⁵ are each independently a hydrogen atom, a $C_1$–$C_8$ alkyl group or a $C_1$–$C_8$ alkylcarbonyl group or both together may form a ring when R⁴ and R⁵ are each a $C_1$–$C_8$ alkyl group.

3. The cyanobiphenyl compound or its salts thereof according to claim 2, wherein, in formula (1), X is a formyl group or the formula:

wherein Y is a chlorine atom, a bromine atom, an iodine atom, —OR² wherein R is a hydrogen atom or 4-piperidinomethyl group wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group, or NHR³ wherein R³ is 4-piperidinomethyl group and wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group.

4. The cyanobiphenyl compound or its salt thereof according to claim 3, wherein, in the above formula (1), X is a formyl group or the formula:

wherein Y is a chlorine atom, a bromine atom, an iodine atom, a hydroxyl group or —NHR³ wherein R³ is 4-piperidinomethyl group and wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group.

5. The cyanobiphenyl derivative or its salts thereof according to claim 4, wherein, in formula (1), X is the formula:

wherein Y is —NHR³ wherein R³ is 4-piperidinomethyl group and wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group.

6. The cyanobiphenyl compound or its salts thereof according to claim 1, wherein, in formula (1), R¹ is a hydrogen atom, a $C_1$–$C_8$ alkyl group, an aryl group or an aralkyl group; X is a carboxyl group, a $C_1$–$C_8$ alkoxycarbonyl group, an aryloxycarbonyl group, aralkoxycarbonyl group, formyl group, the formula:

wherein Y is a chlorine atom, an iodine atom, —OR² wherein R² is a $C_1$–$C_8$ alkylsulfonyl group which may further be substituted with a halogen atom, an arylsulfonyl group or 4-piperidinomethyl group wherein a nitrogen atom in the 4-piperidinomethyl group may be substituted with a $C_5$–$C_8$ alkoxycarbonyl group or an aryloxycarbonyl group, —NHR³ wherein R³ is 4-piperidinomethyl group and wherein a nitrogen atom in the 4-piperidinomethyl group may be substituted with a $C_5$–$C_8$ alkoxycarbonyl group or an aryloxycarbonyl group, the formula:

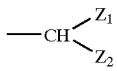

wherein $Z_1$ and $Z_2$ are each independently a chlorine atom, a bromine atom or an iodine atom, or the formula:

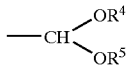

wherein $R^4$ and $R^5$ are each independently a hydrogen atom, a $C_1$–$C_8$ alkyl group or a $C_1$–$C_8$ alkylcarbonyl group or both together may form a ring when $R^4$ and $R^5$ are each a $C_1$–$C_8$ alkyl group.

7. The cyanobiphenyl compound or its salts thereof according to claim 6, wherein, in the above formula (1), $R^1$ is a hydrogen atom or a $C_1$–$C_8$ alkyl group; X is a carboxyl group, a $C_1$–$C_8$ alkoxycarbonyl group, a formyl group, or the formula:

wherein Y is —$OR^2$ wherein $R^2$ is 4-piperidinomethyl group and wherein a nitrogen atom in the 4-piperidinomethyl group may be substituted with a $C_5$–$C_8$ alkoxycarbonyl group or an aryloxycarbonyl group, —$NHR^3$ wherein $R^3$ is 4-piperidinomethyl group and wherein a nitrogen atom in the 4-piperidinomethyl group may be substituted with a $C_5$–$C_8$ alkoxycarbonyl group or an aryloxycarbonyl group.

8. The cyanobiphenyl compound or its salts thereof according to claim 7, wherein, in formula (1), X is a formyl group or the formula:

wherein Y is —$NHR^3$ wherein $R^3$ is 4-piperidinomethyl group and wherein a nitrogen atom in the 4-piperidinomethyl group is substituted with a $C_5$–$C_8$ alkoxycarbonyl group or an aryloxycarbonyl group.

9. A process for preparing a cyanobiphenyl compound represented by the following formula (3):

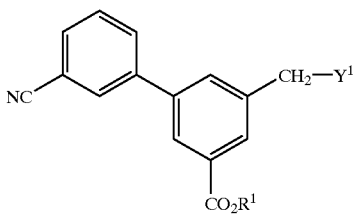

(3)

wherein $R^1$ is as defined in the formula (2); $Y^1$ is —$NHR^3$ wherein $R^3$ is 4-piperidinomethyl group and wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group or its salt thereof, comprising carrying out a dehydration condensation of a compound represented by the following formula (2):

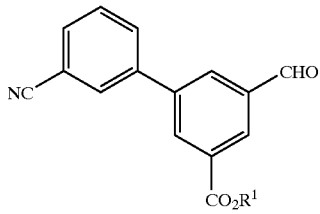

(2)

wherein $R^1$ is a hydrogen atom, a $C_1$–$C_8$ alkyl group, an aryl group or an aralkyl group, with a compound represented by the formula:

$Y^1$—H wherein $Y^1$ is —$NHR^3$ wherein $R^3$ is 4-piperidinomethyl group and wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group, and subsequently conducting a reducing reaction.

10. A process for preparing a cyanobiphenyl compound represented by the following formula (5):

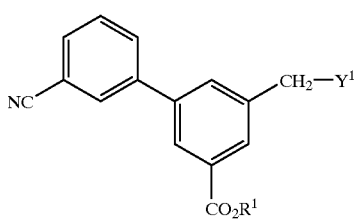

(5)

wherein $R^1$ is as defined in the formula (4); $Y^1$ is —$NHR^3$ wherein $R^3$ is 4-piperidinomethyl group and wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group or its salt, comprising reacting a compound represented by the following formula (4):

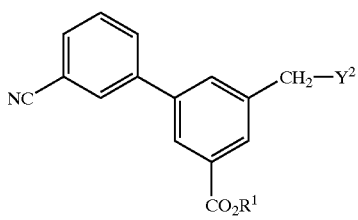

(4)

wherein $R^1$ is a hydrogen atom, a $C_1$–$C_8$ alkyl group, an aryl group or an aralkyl group; $Y^2$ is a chlorine atom, a bromine atom or an iodine atom, with a compound represented by

$Y^1$—H wherein $Y^1$ is —$NHR^3$ wherein $R^3$ is 4-piperidinomethyl group and wherein a nitrogen atom in the 4-piperidinomethyl group may be substituted with a $C_1$–$C_8$ alkyl group, a $C_1$–$C_8$ alkylcarbonyl group, an arylcarbonyl group, a $C_1$–$C_8$ alkoxycarbonyl group, an aryloxycarbonyl group or an aralkoxycarbonyl group.

* * * * *